(12) United States Patent
Tanaka et al.

(10) Patent No.: US 12,116,383 B2
(45) Date of Patent: *Oct. 15, 2024

(54) OLIGOSACCHARIDE C-GLYCOSIDE DERIVATIVES

(71) Applicant: OKINAWA INSTITUTE OF SCIENCE AND TECHNOLOGY SCHOOL CORPORATION, Okinawa (JP)

(72) Inventors: Fujie Tanaka, Okinawa (JP); Sherida Johnson, Okinawa (JP)

(73) Assignee: OKINAWA INSTITUTE OF SCIENCE AND TECHNOLOGY SCHOOL CORPORATION, Okinawa (JP)

(*) Notice: Subject to any disclaimer, the term of this patent is extended or adjusted under 35 U.S.C. 154(b) by 58 days.

This patent is subject to a terminal disclaimer.

(21) Appl. No.: 17/841,241

(22) Filed: Jun. 15, 2022

(65) Prior Publication Data

US 2022/0306671 A1 Sep. 29, 2022

Related U.S. Application Data

(63) Continuation of application No. 17/040,346, filed as application No. PCT/JP2019/011994 on Mar. 22, 2019, now Pat. No. 11,401,293.

(60) Provisional application No. 62/647,241, filed on Mar. 23, 2018.

(51) Int. Cl.
*C07H 7/04* (2006.01)
*C07H 1/00* (2006.01)

(52) U.S. Cl.
CPC ............ *C07H 7/04* (2013.01); *C07H 1/00* (2013.01)

(58) Field of Classification Search
None
See application file for complete search history.

(56) References Cited

U.S. PATENT DOCUMENTS

| 8,314,219 B1 | 11/2012 | Price |
| 2008/0081905 A1 | 4/2008 | Price |
| 2008/0153760 A1 | 6/2008 | Leroy et al. |
| 2008/0193400 A1 | 8/2008 | Dalko et al. |
| 2011/0245490 A1 | 10/2011 | Benvegnu et al. |

FOREIGN PATENT DOCUMENTS

| WO | 02/051803 | 7/2002 |
| WO | 2016/151989 | 9/2016 |

OTHER PUBLICATIONS

International Search Report issued Jun. 18, 2019 in International (PCT) Application No. PCT/JP2019/011994.
Carpenter et al., "Preparation of saturated and unsaturated fatty acid hydrazides and long chain C-glycoside ketohydrazones", Green Chem., 2010, vol. 12, pp. 2012-2018.
Bisht et al., "Synthetic studies in butenonyl C-glycosides: Preparation of polyfunctional alkanonyl glycosides and their enzyme inhibitory activity", Bioorganic & Medicinal Chemistry Letters, vol. 19, 2009, pp. 2699-2703.
Rodrigues et al., "A convenient, one-step, synthesis of β-C-glycosidic ketones in aqueous media", Chem. Commun., 2000, pp. 2049-2050.
Wei et al., "Copper(I)-Catalyzed Dehydrative C-Glycosidation of Unprotected Pyranoses with Ketones", ACS Catal. 2016, vol. 6, pp. 6718-6722.
Ranoux et al., "Horner-Wadsworth-Emmons Reaction of Unprotected Sugars in Water or in the Absence of Any Solvent: One-Step Access to C-Glycoside Amphiphiles", Eur. J. Org. Chem, 2010, pp. 1314-1323.
Cavezza et al., "Synthesis of Pro-Xylane™: A new biologically active C-glycoside in aqueous media", Bioorganic & Medicinal Chemistry Letters, vol. 19, 2009, pp. 845-849.
Feng et al., "Microwave-assisted efficient synthesis of aryl ketone β-C-glycosides from unprotected aldoses", Carbohydrate Research, vol. 346, 2011, pp. 352-356.
Feng et al., "Concise synthesis of β-glucosidase inhibitors α-bromoacetone-βC-giycooides", Huaxue Shiji, 2013, vol. 35, No. 6, pp. 561-563; 566.

(Continued)

*Primary Examiner* — Layla D Berry
(74) *Attorney, Agent, or Firm* — Wenderoth, Lind & Ponack, L.L.P.

(57) ABSTRACT

The present invention provides a novel process for preparing an oligosaccharide C-glycoside derivative of formula I, comprising reacting a compound of formula II with compound of formula III in the presence of at least one primary or secondary amine and at least one additive [in the formulae, the substituents are as defined herein], and novel oligosaccharide C-glycoside derivatives that can be prepared using the process.

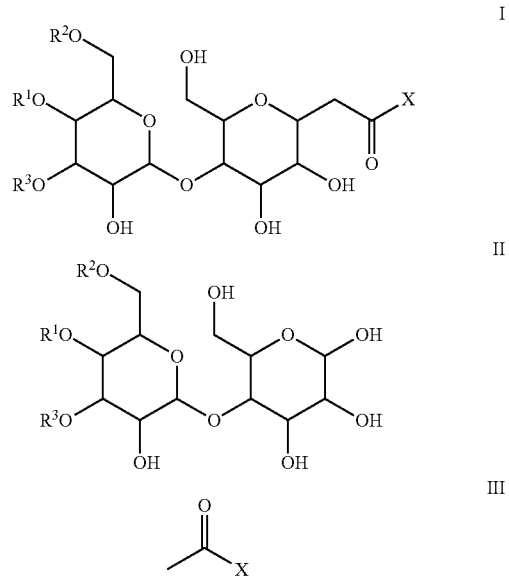

6 Claims, No Drawings

(56) References Cited

OTHER PUBLICATIONS

Hersant et al., "One-step synthesis of β-C-glycolipid derivatives from unprotected sugars", Carbohydrate Research, vol. 339, 2004, pp. 741-745.
Howard et al., "Bromoketone C-Glycosides, a New Class of β-Glucanase Inactivators", J. Am. Chem. Soc., 1998, vol. 120, pp. 10326-10331.
Zhdanov et al., "Reaction of partially substituted aldoses with p-methoxybenzoylmethylenephosphorane", Journal of General Chemistry of the USSR, vol. 39, No. 1, Jan. 1969, pp. 119-122, with translation.
Fenger et al., "Synthesis and Analysis of Specific Covalent Inhibitors of endo-Xyloglucanases", Chem Bio Chem, 2015, vol. 16, pp. 575-583.
Johnson et al., "Direct synthesis of C-glycosides from unprotected 2-N-acyl-aldohexoses via aldol condensation-oxa-Michael reactions with unactivated ketones", Org. Biomol. Chem., 2016, vol. 14, pp. 259-264.
Johnson et al., "C-Glycosidation of Unprotected Di- and Trisaccharide Aldopyranoses with Ketones Using Pyrrolidine-Boric Acid Catalysis", J. Org. Chem., 2018, vol. 83, pp. 4581-4597.
CAS Registry No. 906797-25-9, Sep. 15, 2006. (Year: 2006).
Bisht, Carbohydrate Research 343 (2008) 1399-1406. (Year: 2008).

OLIGOSACCHARIDE C-GLYCOSIDE DERIVATIVES

TECHNICAL FIELD

The present invention relates to a process for preparing oligosaccharide C-glycoside derivatives, novel oligosaccharide C-glycoside derivatives that can be prepared using such process, use thereof as a therapeutically active substance, and pharmaceutical compositions comprising such oligosaccharide C-glycoside derivatives. The present invention also relates to the oligosaccharide C-glycosidation method and the oligosaccharide C-glycoside derivatives that are used for conjugation or covalent attachment of the oligosaccharides to other surface of assay plate wells and to other molecules, which are used for diagnosis methods and/or as therapeutics and molecular probes used in diagnostics and in biomedical research.

BACKGROUND ART

Carbohydrates play important roles in biological systems and thus the synthesis of carbohydrate derivatives is of interest for the development of bioactives, probes, and other functional molecules. C-Glycosidation, the C-C bond formation reaction at the anomeric carbon, of unprotected carbohydrates is an important reaction for the synthesis of carbohydrate-derived pharmaceuticals, glycoconjugates, and other functional carbohydrate derivatives. However, direct C-glycosidation reactions of unprotected carbohydrates are often difficult, and the C-C bond formation reaction of unprotected carbohydrates has been considered as a task of enzymes. One of the difficulties in the reactions of unprotected carbohydrates may be the presence of polyhydroxy groups in the carbohydrates. In many reactions of carbohydrates, hydroxy groups must be firstly protected to avoid that acidic protons of the hydroxy groups react with reagents and/or that the hydroxy groups interrupt hydrogen bonding necessary for the catalysis and stereocontrol. Another difficulty with direct C-glycosidation reactions of unprotected carbohydrates lies in the cyclic hemiacetal form of the aldoses. Although the aldehyde carbonyl group of the aldoses may be a good site to react with nucleophiles, the generation of the aldehyde group from the cyclic hemiacetal forms by opening the hemiacetal ring, especially from 6-membered hemiacetal forms of aldohexose derivatives, is not easy under mild reaction conditions that do not affect the functional groups of the carbohydrates and of the reactants used for the C-glycosidation reactions. Therefore, many non-enzymatic chemical C-glycosidation reactions of carbohydrates have been performed on pre-activated forms of carbohydrates with protected hydroxy groups or on specific precursors bearing functional groups for the bond formation at the anomeric carbons. Considering atom- and step-economy, direct reactions on unprotected carbohydrates are more preferable than reactions which require protection and deprotection steps and/or strategies requiring the synthesis of pre-activated forms for the reactions at the anomeric carbons.

SUMMARY OF INVENTION

Technical Problem

C-glycosidation reactions that have been reported of unprotected carbohydrates include reactions with relatively highly reactive nucleophiles, such as β-diketones, β-keto esters and related molecules, nitromethane, cyanide, and Wittig and related reagents. C-Glycosidation reactions of unprotected carbohydrates also include reactions with metal-activated reagents. Whereas these reactions have afforded C-glycosidation products from certain unprotected carbohydrates, these reactions have limitations. For example, the reactions with β-diketones can be used only for the synthesis of acetone-attached and related C-glycosides because of the use of β-diketones as nucleophiles and because of the use of basic conditions under heating. Functional groups that are not suited to the synthesis of the β-diketones and/or to the basic and heating C-glycosidation conditions cannot be introduced directly.

Recently C-glycosidation reactions of unprotected carbohydrates with simple ketones have been reported. However, these reported reaction methods were mostly developed for monosaccharides.

There are approximately two or three times more hydroxy groups per molecule in di- and trisaccharides, respectively, as in monosaccharides. Because of this and/or because of other reasons, reaction catalysts and conditions that work for C-glycosidation of unprotected monosaccharides do not always work efficiently for disaccharides. Thus, to directly synthesize functionalized C-glycosides from unprotected di- and trisaccharides, advances were required.

Solution to Problem

The present inventors have found that oligosaccharide C-glycoside derivatives can be prepared under high stereoselective, mild, and atom-economical conditions by the C-glycosidation reaction of di- and trisaccharide aldopyranoses with ketones using pyrrolidine-boric acid catalyst systems.

In summary, the followings can be provided by the present invention.

(1) A process for preparing a compound of formula I

[Chem.1]

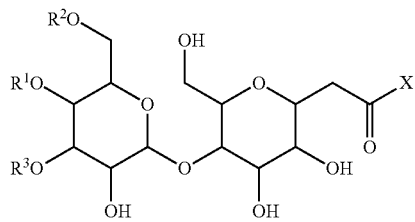

comprising
reacting a compound of formula II

[Chem.2]

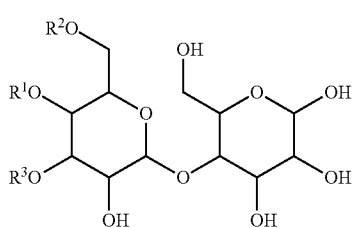

with a compound of formula III

[Chem.3]

III wherein

X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted, $R^1$ is H, or a sugar residue, $R^2$ is H, or a sugar residue, and $R^3$ is H, or a sugar residue, in the presence of at least one primary or secondary amine and at least one additive.

(2) A process for preparing a compound of I-1

[Chem.4]

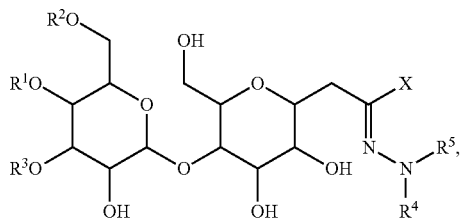
I-1 comprising
reacting a compound of formula II

[Chem.5]

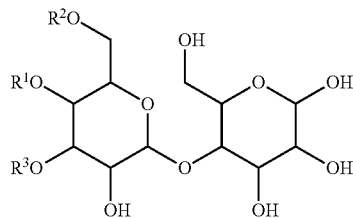
II with a compound of formula III

[Chem.6]

III in the presence of at least one primary or secondary amine and at least one additive to give a compound of formula I

[Chem.7]

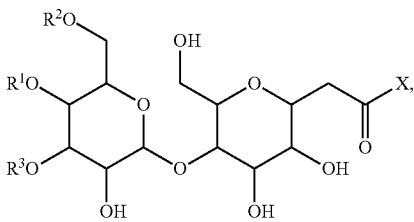
I and
reacting the compound of formula I with a reactant, wherein

X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted, $R^1$ is H, or a sugar residue, $R^2$ is H, or a sugar residue, $R^3$ is H, or a sugar residue, $R^4$ and $R^5$ independently from each other are selected from the group consisting of H, and $C_{1-7}$alkyl, phenyl, benzyl, piperidinyl, p-tosyl, and 1-phthalazinyl, which are optionally substituted.

(3) A process for preparing a compound of formula I-1'

[Chem.8]

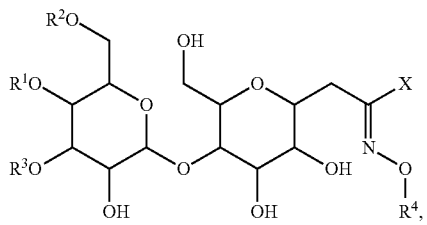
I-1' comprising
reacting a compound of formula II

[Chem.9]

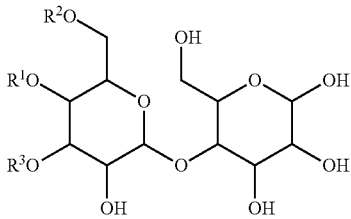
II with a compound of formula III

[Chem.10]

III in the presence of at least one primary or secondary amine and at least one additive to give a compound of formula I

[Chem.11]

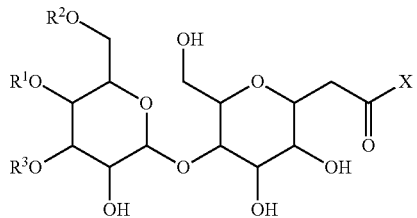

I and
reacting the compound of formula I with a reactant, wherein

X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$-alkyl, ($C_{1-7}$alkoxycarbonyl)-$C_{1-7}$alkyl, $C_{2-7}$alkynyl-$C_{1-7}$alkyl, or aryl, which are optionally substituted, $R^1$ is H, or a sugar residue, $R^2$ is H, or a sugar residue, $R^3$ is H, or a sugar residue, and $R^4$ is H, or $C_{1-7}$alkyl, phenyl, benzyl, piperidinyl, p-tosyl, or 1-phthalazinyl, which are optionally substituted.

(4) A process for preparing a compound of formula I-2

[Chem.12]

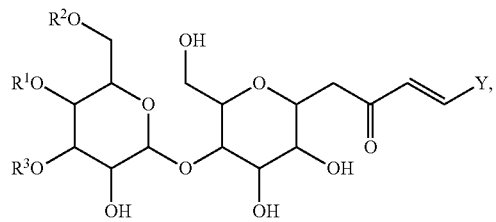

I-2 comprising
reacting a compound of formula II

[Chem.13]

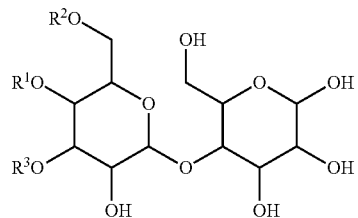

II with a compound of formula III

[Chem.14]

III in the presence of at least one primary or secondary amine and at least one additive to give a compound of formula I

[Chem.15]

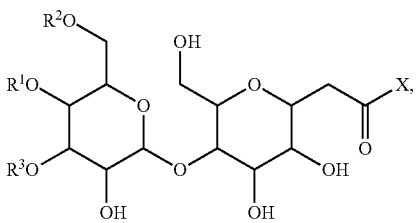

I and
reacting the compound of formula I with a reactant, wherein

X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted, $R^1$ is H, or a sugar residue, $R^2$ is H, or a sugar residue, $R^3$ is H, or a sugar residue, and Y is optionally substituted aryl.

(5) The process according to any of the above-described (1)-(4), wherein the at least primary or secondary amine and the at least one additive are selected from (a) pyrrolidine and $H_3BO_3$, (b) pyrrolidine and $B(OMe)_3$, and (c) benzylamine and $H_3BO_3$.

(6) A compound of any one of formulae I, I-1, I-1', and I-2, whenever manufactured according to the process of any of the above-described (1) to (5), or a salt thereof,

[Chem.16]

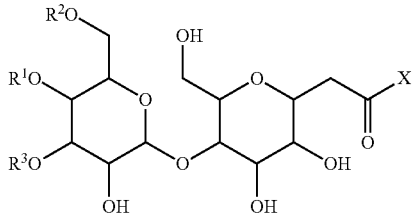

I

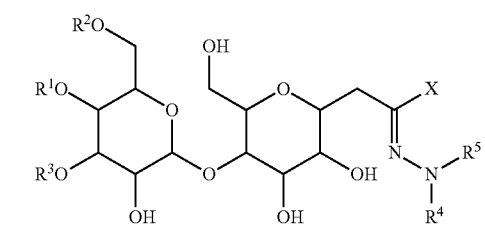

I-1

-continued

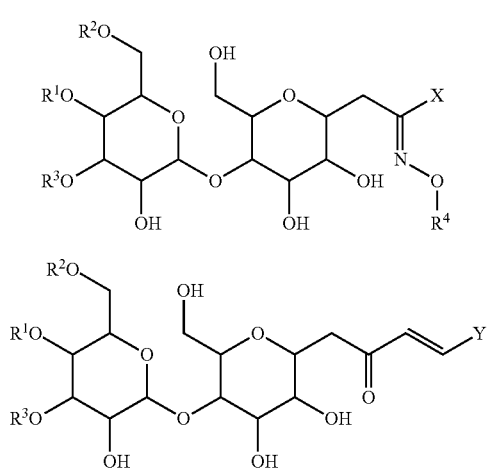

wherein

X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted, $R^1$ is H, or a sugar residue, $R^2$ is H, or a sugar residue, $R^3$ is H, or a sugar residue, and $R^4$ and $R^5$ independently from each other are selected from the group consisting of H, and $C_{1-7}$alkyl, phenyl, benzyl, piperidinyl, p-tosyl, 1-phthalazinyl, and which are optionally substituted, and Y is optionally substituted aryl.

(7) The compound according to the above-described (4) or a salt thereof, wherein the compound is of formula I-1, I-1', or I-2.

(8) The compound according to the above-described (4) or a salt thereof, wherein the compound is selected from

[Chem.17]

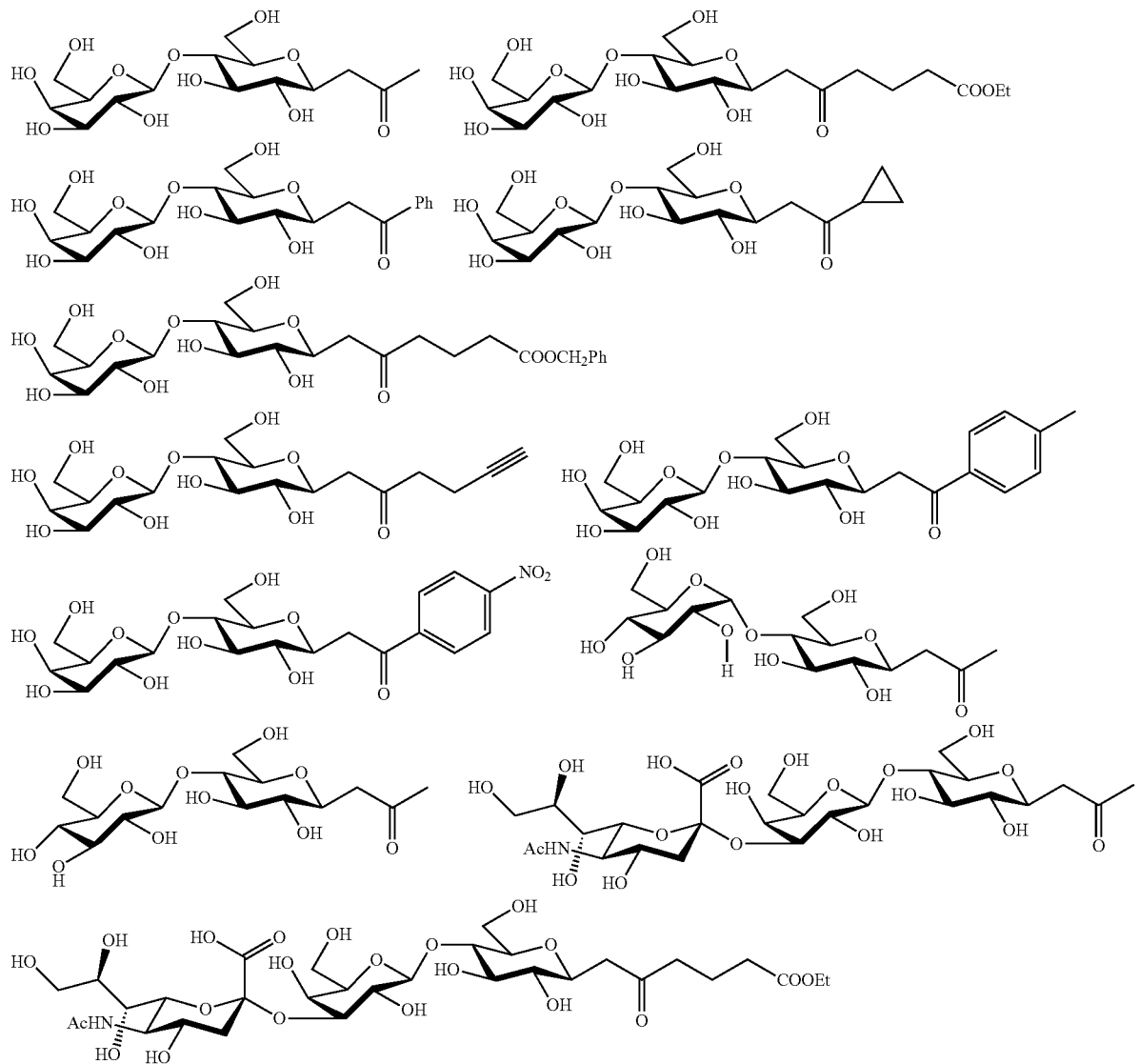

-continued
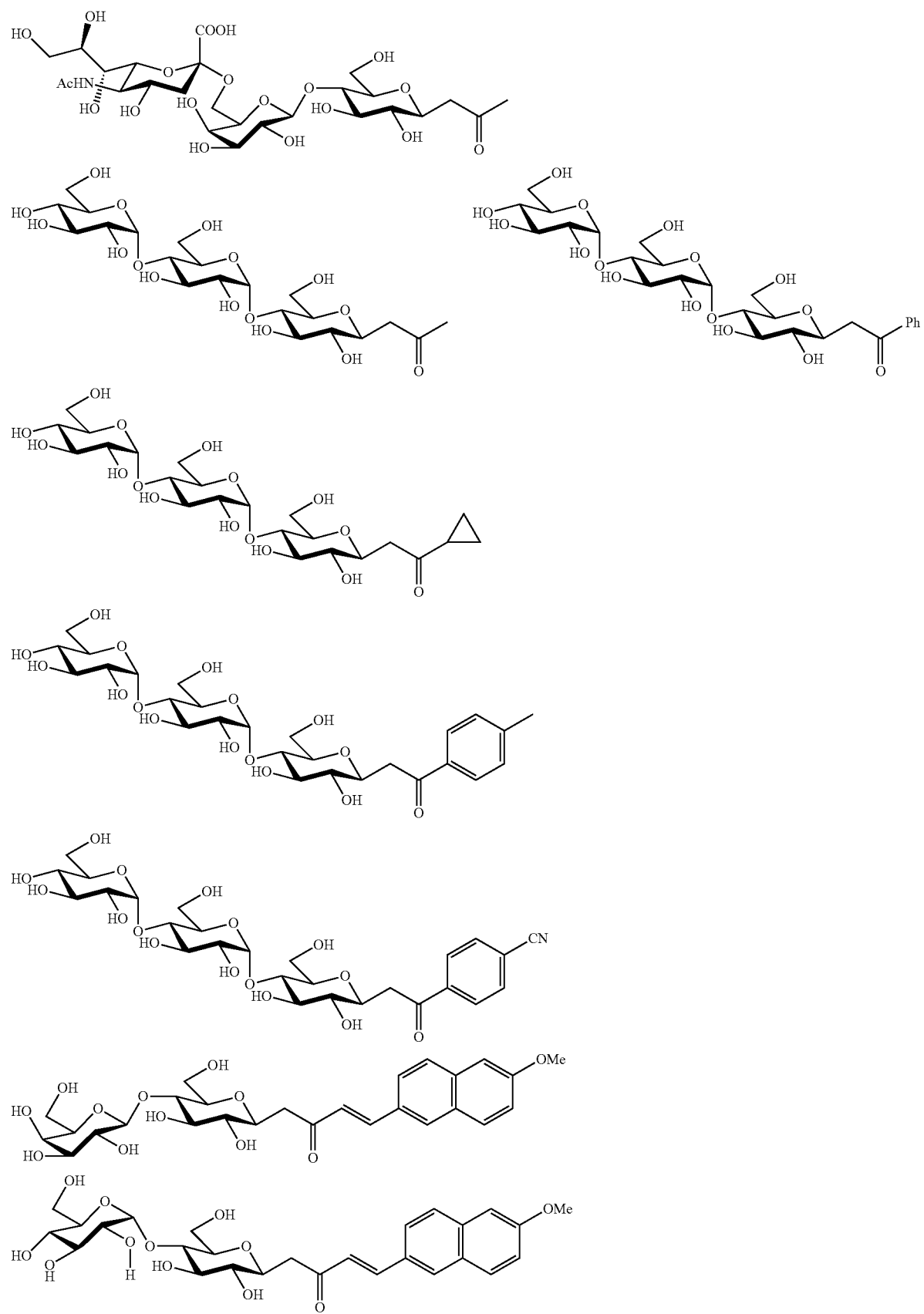

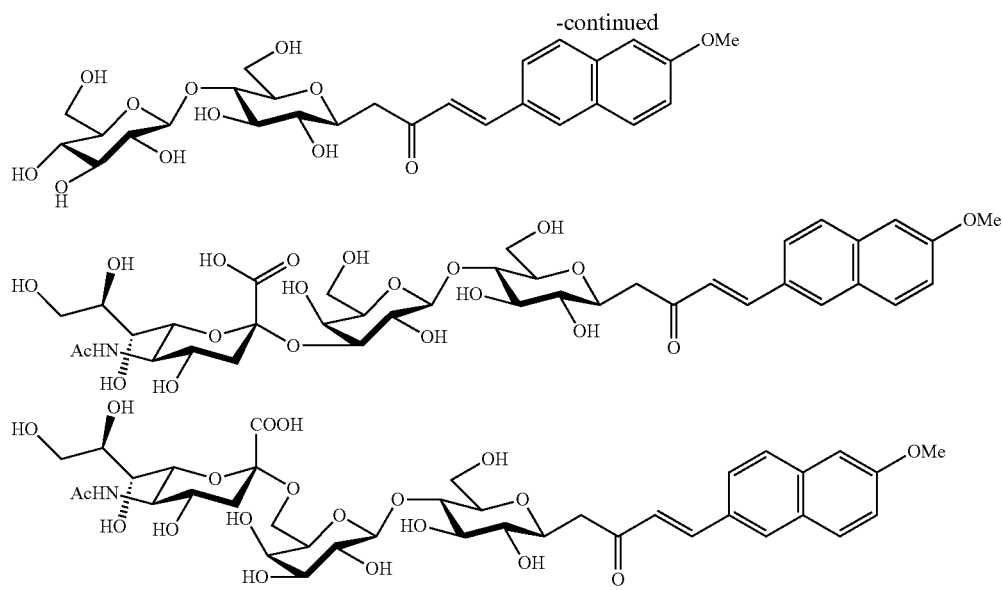

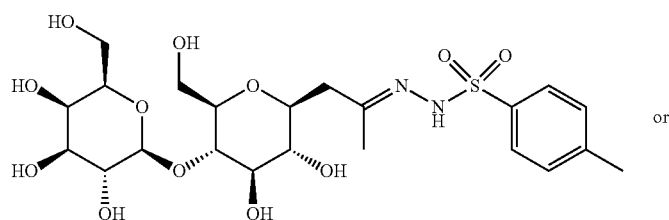

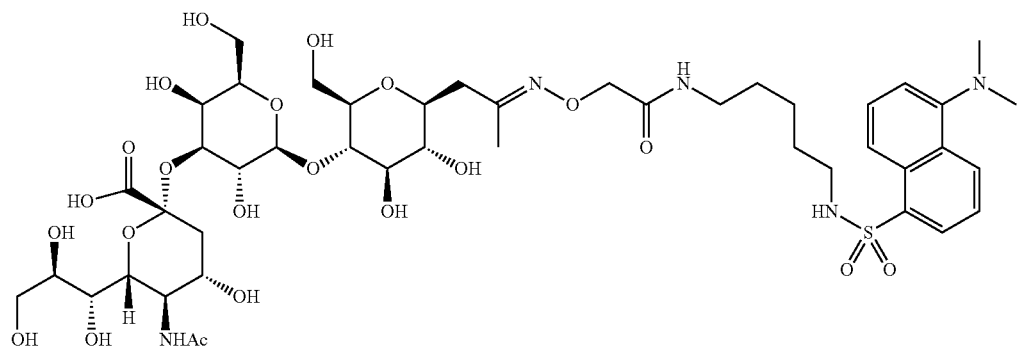

(9) A pharmaceutical composition, comprising the compound according to any of the above-described (6) to (8) or a pharmaceutically acceptable salt thereof and a pharmaceutically acceptable carrier.

DESCRIPTION OF EMBODIMENTS

One embodiment of the present invention provides a process for preparing a compound of formula I, i.e. an oligosaccharide C-glycoside derivative,

[Chem.18]

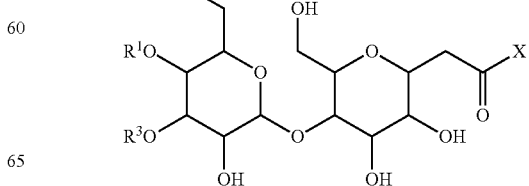

comprising
reacting a compound of formula II

[Chem.19]

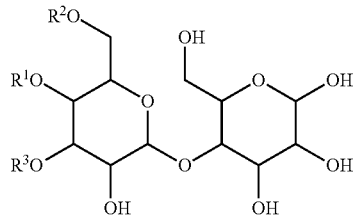

II with a compound of formula III

[Chem.20]

III wherein
X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted,
$R^1$ is H, or a sugar residue,
$R^2$ is H, or a sugar residue, and
$R^3$ is H, or a sugar residue,
in the presence of at least one primary or secondary amine and at least one additive.

The amount of each compound used in the process of the present invention can be at any amount as long as the reaction can proceed and the present invention can be carried out. The molar ratio of the compound of formula III to the compound of formula II is, for example, 2 to 100, preferably 4 to 40, and more preferably 4 to 30. The molar ratio of the total molar amount of the at least primary or secondary amine to the molar amount of the compound of formula II is, for example, 0.05 to 1.0, preferably 0.1 to 0.8, and more preferably 0.4 to 0.6. The molar ratio of the total molar amount of the at least one additive to the molar amount of the compound of formula II is, for example, 0.05 to 5.0, preferably 0.2 to 3.0, and more preferably 1.0 to 2.0.

The above reaction can be carried out in any solvent as long as the reaction can proceed and the present invention can be carried out. Examples of the solvents include, but are not limited to, polar solvents such as MeOH, DMSO, and the like. The reaction time is not particularly limited but, for example, for 12 to 120 hours, preferably for 12 to 96 hours, and more preferably for 24 to 96 hours. The above reaction temperature can be, for example, at 10-60° C., preferably at 15-40° C., and more preferably at 20-30° C.

The term "$C_{1-7}$alkyl" as used herein denotes a monovalent linear or branched saturated hydrocarbon group having 1 to 7 carbon atoms, preferably 1 to 4 carbon atoms. Examples of $C_{1-7}$alkyl include, but are not limited to, methyl, ethyl, n-propyl, isopropyl, n-butyl, isobutyl, sec-butyl, tert-butyl, pentyl, hexyl, and heptyl. Preferable are methyl, ethyl, n-propyl, isopropyl, n-butyl, isobutyl, sec-butyl, tert-butyl, n-pentyl, and isopentyl, and more preferable are methyl, ethyl, propyl, isopropyl, isobutyl, tert-butyl, and isopentyl.

The term "$C_{3-7}$cycloalkyl" as used herein denotes a monovalent saturated carbocyclic group having 3 to 7 carbon atoms, preferably 3 to 6 carbon atoms, as ring atoms. Examples of $C_{3-7}$cycloalkyl include, but are not limited to, cyclopropyl, cyclobutyl, cyclopentyl, and cyclohexyl.

The term "halo-$C_{1-7}$alkyl" as used herein denotes the $C_{1-7}$alkyl of which at least one carbon atom is substituted with halogen(s). When two or more halogens are substituted to the same carbon atom or different carbon atoms, the halogens may be same or different. Preferable is substitution with 1 to 5 halogen atoms, and more preferable is substitution with 1 to 3 halogen atoms. Examples of halogen include, but are not limited to, fluorine, chlorine, bromine, and iodine. Preferable are fluorine, chlorine, and bromine, and more preferable are fluorine and chlorine. Examples of halo-$C_{1-7}$alkyl include, but are not limited to, fluoromethyl, difluoromethyl, trifluoromethyl, 1,1,1-trifluoroethyl, 1,1,1-trifluoropropyl, and pentafluoroethyl.

The term "$C_{1-7}$alkoxy" as used herein denotes a group in which an oxygen atom is linked to the $C_{1-7}$alkyl. $C_{1-7}$alkoxy can be shown by the formula of $C_{1-7}$alkyl-O—. Examples of $C_{1-7}$alkoxy include, but are not limited to, methoxy, ethoxy, n-propoxy, isopropoxy, n-butoxy, isobutoxy, sec-butoxy, and tert-butoxy.

The term "halo-$C_{1-7}$alkoxy" as used herein denotes the $C_{1-7}$alkoxy of which at least one carbon atom is substituted with halogen(s). When two or more halogens are substituted to the same carbon atom or different carbon atoms, the halogens may be same or different. Preferable is substitution with 1 to 5 halogen atoms, and more preferable is substitution with 1 to 3 halogen atoms. Examples of halogen include, but are not limited to, fluorine, chlorine, bromine, and iodine. Preferable are fluorine, chlorine, and bromine, and more preferable are fluorine and chlorine. Examples of halo-$C_{1-7}$ alkoxy include, but are not limited to, fluoromethoxy, difluoromethoxy, trifluoromethoxy, 1,1,1-trifluoroethoxy, 1,1,1-trifluoropropoxy, and pentafluoroethoxy.

The term "$C_{1-7}$alkoxy-$C_{1-7}$alkyl" as used herein denotes the $C_{1-7}$alkyl of which at least one carbon atom is substituted with the $C_{1-7}$alkoxy. Examples of the $C_{1-7}$alkoxy-$C_{1-7}$ alkyl include, but are not limited to, methoxymethyl, dimethoxymethyl, tetrahydrofuran-3-yl-methyl, and tetrahydropyran-4-yl-methy.

The term "$C_{1-7}$alkoxycarbonyl" as used herein denotes a group in which $C_{1-7}$alkoxy is bonded with —CO— group. The $C_{1-7}$alkoxycarbonyl can be shown by the formula of $C_{1-7}$ alkoxy-CO—.

The term "($C_{1-7}$alkoxycarbonyl)-$C_{1-7}$alkyl" as used herein denotes the $C_{1-7}$alkyl of which at least one carbon atom is substituted with at least one $C_{1-7}$alkoxycarbonyl. Examples of optionally substituted ($C_{1-7}$alkoxycarbonyl)-$C_{1-7}$alkyl include, but are not limited to methoxycarbonyl-methyl, ethoxycarbonyl-metyl, methoxycarbonyl-ethyl, ethoxycarbonyl-ethyl, methoxycarobnyl-propyl, ethoxycarbonyl-propyl, methoxy-carbonyl-butyl, ethoxycarbonyl-butyl, and benzyloxycarbonyl-propyl, and preferable are 2-(ethoxycarbonyl)-1-ethyl, 3-(methoxycarbonyl)-1-propyl, 3-(ethoxycarbonyl)-1-propyl, 4-(ethoxycarbonyl)-1-butyl, and 3-(benzyloxycarbonyl)-1-propyl, The term "$C_{2-7}$alkynyl" as used herein denotes a monovalent linear or branched hydrocarbon group containing a C-C triple bond and having 2 to 7 carbon atoms, preferably 4 to 6 carbon atoms. Examples of $C_{2-7}$alkynyl include, but are not limited to, ethynyl, propynyl, butynyl, pentynyl, hexynyl, and heptynyl. Preferable are butynyl, and hexynyl, and more preferable are but-3-ynyl and hex-5-ynyl.

The term "$C_{2-7}$alkynyl-$C_{1-7}$alkyl" as used herein denotes the $C_{1-7}$alkyl of which at least one carbon atom is substituted with at least one $C_{2-7}$ alkynyl. Example of the $C_{2-7}$ alkynyl-C1-7alkyl include, but are not limited to di(but-3-ynyl) methyl, 2,2-di(hex-5-ynyl)ethyl, 3,5-di(hex-5-ynyl)cyclohexyl, and 2-(but-3-ynyl)propyl.

The term "aryl" as used herein denotes a monovalent aromatic carbocyclic or heterocyclic group. Examples of optionally substituted aryl include, but are not limited to phenyl, phenyl substituted with $C_{1-7}$, nitro, halogen, and the like, thiophenyl, furanyl, benzofuranyl, naphthyl, and quinolinyl, and preferable are phenyl, 4-methylphenyl, 4-nitrophenyl, 4-bromophenyl, thiophen-2-yl, furan-2-yl, benzofuran-2-yl, naphth-1-yl, naphth-2-yl, and quinolin-3-yl.

The term "sugar residue" as used herein refers to a substituent which is derived from a sugar and in which one of OH group does not exist in order to form a bonding site. The sugar can be monosaccharide, disaccharide, oligosaccharide, or polysaccharide, which are optionally substituted. The saccharide can include aminosaccharide. Examples of the sugar residue include, but are not limited to a glucose residue, a sialic acid reside, and other carbohydrate resides.

The term "glucose residue" as used herein refers to a substituent which is derived from glucose and in which one of OH group in glucose does not exist and such site becomes a bonding site. For example, the glucose residue can be a glucosyl group. Examples of the glucosyl group include, but are not limited to, β-D-glucosyl, α-D-glucosyl, β-L-glucosyl, and α-L-glucosyl.

The term "sialic acid residue" as used herein refers to a substituent which is derived from sialic acid and in which one of OH group in sialic acid does not exist and such site becomes a bonding site. For example, the sialic acid residue can be a sialyl group. Examples of the glucosyl group include, but are not limited to, β-sialyl and α-sialyl.

Examples of other carbohydrate residue include, but are not limited to β-D-mannosyl, α-D-mannosyl, β-D-galactosyl, α-D-galactosl, N-acetyl-β-D-mannosaminyl, N-acetyl-α-D-mannosaminyl, N-acetyl-β-D-glucosaminyl, N-acetyl-α-D-glucoosaminyl, N-acetyl-β-D-galactosaminyl, N-acetyl-α-D-galactosaminyl, glucosyl-glucosyl, glucosyl-mannosyl, glucosyl-galactosyl, mannosyl-glucosyl, galactosyl-glucosyl, N-acetyl-α-D-mannosaminyl-glucosyl, and sialyl-lactosyl.

As the "primary or secondary amine" in the above-described process, any primary or secondary amine can be used as long as the reaction can proceed and the present invention can be carried out. Such primary or secondary amines include, but are not limited to, aliphatic amines (e.g., benzylamine, methylamine, dimethylamine, ethylamine, diethylamine, and the like), heterocyclic amines (e.g., pyrrolidine, piperidine, piperazine, morpholine, and the like), and a combination thereof. Preferable are 5- or 6-membered heterocyclic primary or secondary amines, and primary amines such as benzylamine, and more preferable is pyrrolidine.

As the "additive" in the present invention, any additive can be used as long as the process can proceed and the present invention can be carried out. Such additives include, but are not limited to, boric acid (e.g., $H_3BO_3$), boric compounds, and a combination thereof. The boric compounds include, but are not limited to, trimethyl borate (e.g., $B(OMe)_3$). Preferable are boric acid and trimethyl borate, and more preferable is boric acid.

Another embodiment of the present invention provides a process for preparing a compound of I-1

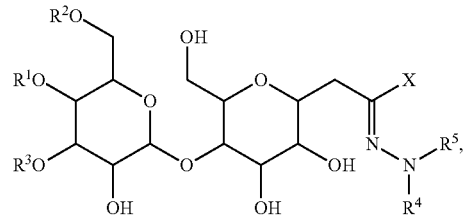

comprising reacting a compound of formula II

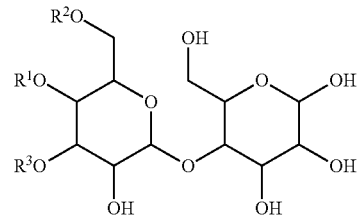

with a compound of formula III

in the presence of at least one primary or secondary amine and at least one additive to give a compound of formula I

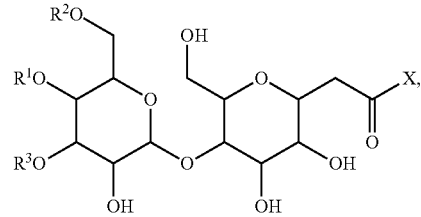

and reacting the compound of formula I with a reactant, wherein

X, $R^1$, $R^2$, and $R^3$ are as defined above, and $R^4$ and $R^5$ independently from each other are selected from the group consisting of H, and $C_{1-7}$alkyl, phenyl, benzyl, piperidinyl, p-tosyl, and 1-phthalazinyl, which are optionally substituted.

Still another embodiment of the present invention provides a process for preparing a compound of formula I-1'

[Chem.25]

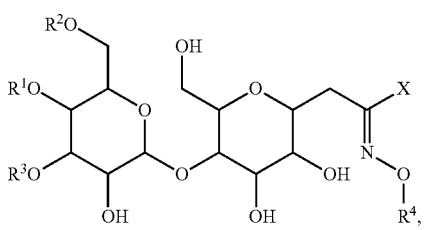

I-1' comprising
reacting a compound of formula II

[Chem.26]

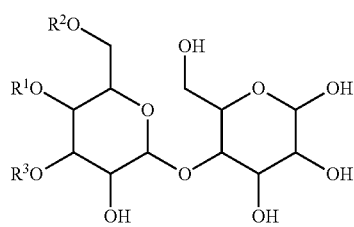

II with a compound of formula III

[Chem.27]

III in the presence of at least one primary or secondary amine and at least one additive to give a compound of formula I

[Chem.28]

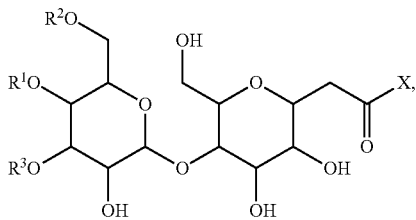

I and
reacting the compound of formula I with a reactant, wherein
X, $R^1$, $R^2$, and $R^3$ are as defined above, and
$R^4$ is H, or $C_{1-7}$alkyl, phenyl, benzyl, piperidinyl, p-tosyl, or 1-phthalazinyl, which are optionally substituted.

The "reactant" used in the above reaction can be a hydrazine derivative. The hydrazine derivatives include, but are not limited to, methylhydrazine, dimethyl-hydrazine, phenylhydrazine, benzylhydrazine, piperidinehydrazine, p-tosylhydrazine, 1-phthalazinylhydrazine, and the like, and preferable is p-tosyl hydrazine. The amount of the reactant to be used is not particularly limited as long as the reaction can proceed and the present invention can be carried out.

The above reaction can be carried out in any solvent as long as the reaction can proceed and the present invention can be carried out. Such solvents include, but are not limited to DMF, DMSO, EtOH, MeOH, THF, and the like. The reaction time is not particularly limited as long as the reaction can proceed and the present invention can be carried out but is, for example, for 10 to 24 hours. The above reaction can be carried out, for example, at 0 to 40° C.

Still yet another embodiment of the present invention provides a process for preparing a compound of formula I-2

[Chem.29]

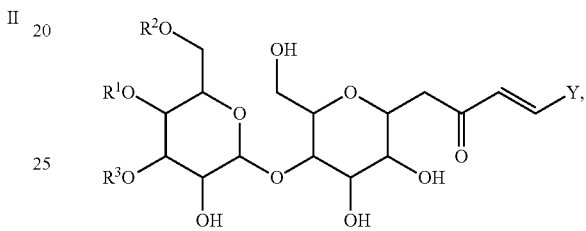

I-2 comprising
reacting a compound of formula II

[Chem.30]

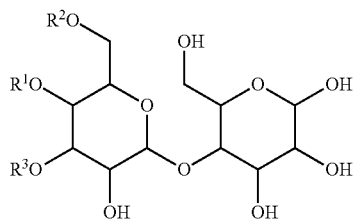

II with a compound of formula III

[Chem.31]

III in the presence of at least one primary or secondary amine and at least one additive to give a compound of formula I

[Chem.32]

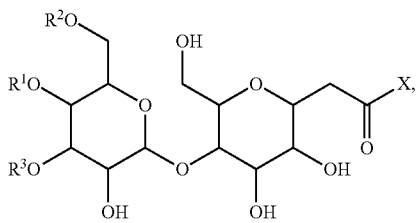

I and reacting the compound of formula I with a reactant, wherein

X, $R^1$, $R^2$, and $R^3$ are defined above, and

Y is optionally substituted aryl, in particular 6-methoxynaphth-2-yl.

The "reactant" used in the above reaction can be 6-methoxy-2-naphthaldehyde, or arylaldehydes. The amount of the reactant to be used is not particularly limited as long as the reaction can proceed and the present invention can be carried out.

The above reaction can be carried out using catalysts (such as L-proline-i-$Pr_2NEt$, and pyrrolidine-boric acid) in any solvent (such as DMSO) as long as the reaction can proceed and the present invention can be carried out.

When any one of X, $R^1$ to $R^5$ and Y has an optional substituent, such substituent can be independently from each other and selected from, for example, halogen, C1-7alkyl, C1-7alkoxy, aryl, nitro, cyano, amino, benzyloxycarbonylamino, tert-butoxycarbonylamino, ester, amide, and the like.

In preferable embodiments of the present invention, the at least one primary or secondary amine and the at least one additive are selected from (a) pyrrolidine and $H_3BO_3$,
(b) pyrrolidine and $B(OMe)_3$, and
(c) benzylamine and $H_3BO_3$.

In one aspect, the present invention provides novel compounds shown by any one of formulae I, I-1, I-1', and I-2, and such compounds can be manufactured according to the process as described hereinbefore, or a salt thereof,

[Chem.33]

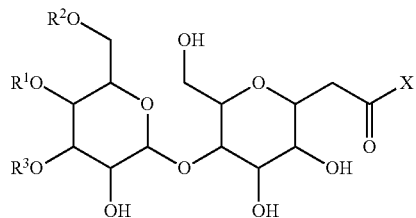

I

[Chem.34]

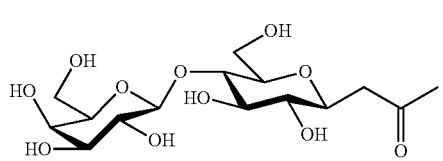

5aa

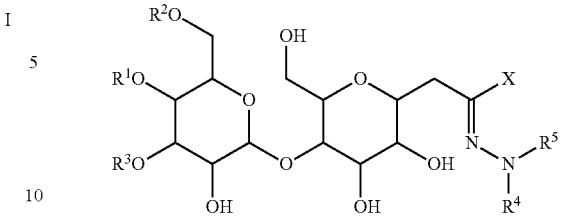

I-1

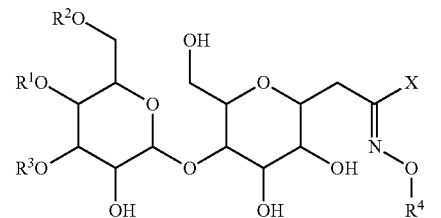

I-1'

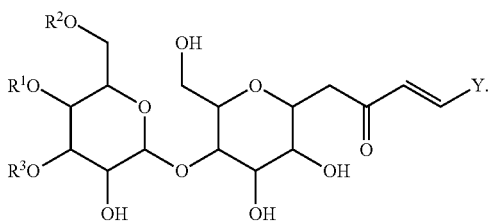

I-2

In these formulae, each symbol has the same meaning as defined hereinabove.

The compounds of formula I I-1, I-1', and I-2 may contain several asymmetric centers and be present in the form of enantiomerically pure single enantiomers, mixtures of enantiomers (e.g., racemates) of single diastereomers, enantiomerically pure forms of diastereoisomer mixtures, mixtures of diastereoisomers, single di-astereoisomer racemates, or mixtures of diastereoisomeric mixtures' racemates. The optically pure form can be obtained by, for example, reactions of enantiomerically pure forms of II, optical resolution of the racemates, asymmetric synthesis, or asymmetric chromatography (e.g., chromatography using a chiral carrier or eluent).

In one embodiment of the above aspect, the compound is the compound of formula I-1, I-1', I-2, or a salt thereof.

In another embodiment of the above aspect, the compound is selected from the followings, or a salt thereof:

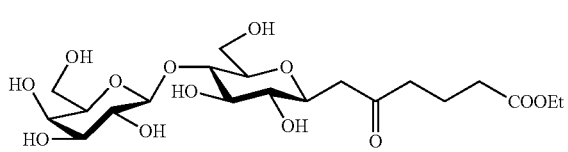

5ab

-continued
5ac 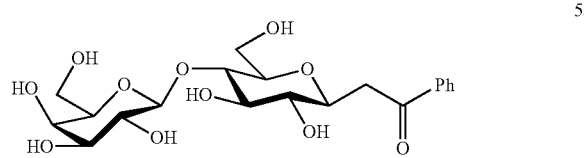
5ad 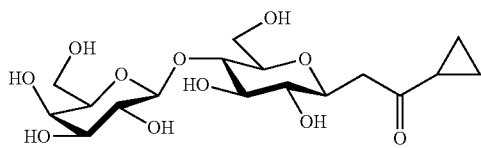
5ae 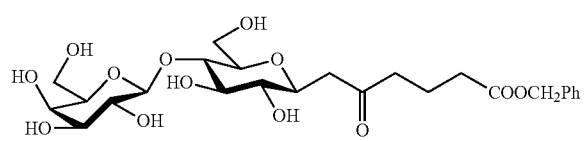
5af 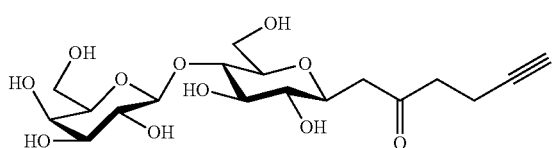
5ag 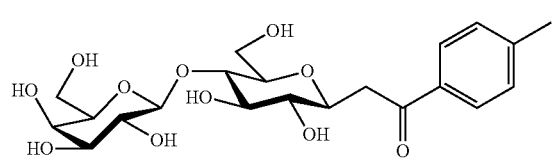
5ah 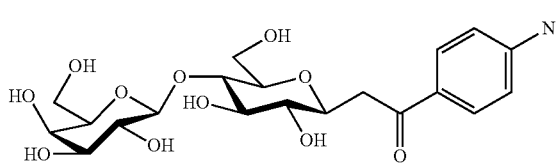
5ba 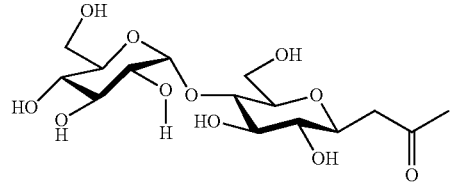
5ca 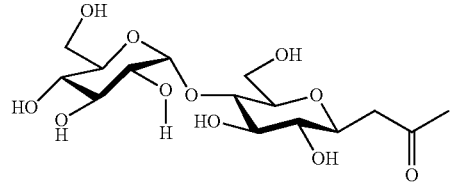
7aa 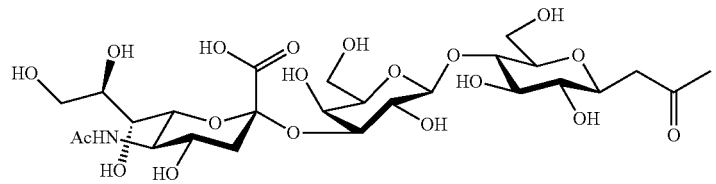
7ab 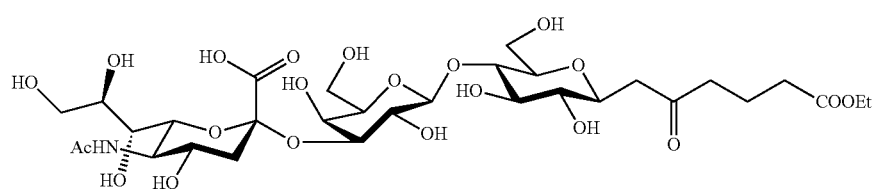
7ba 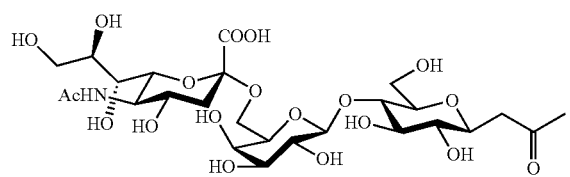
7ca 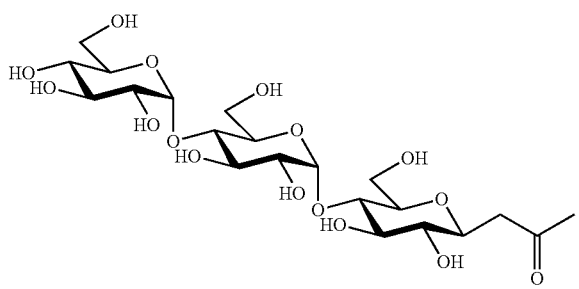

-continued
7cc
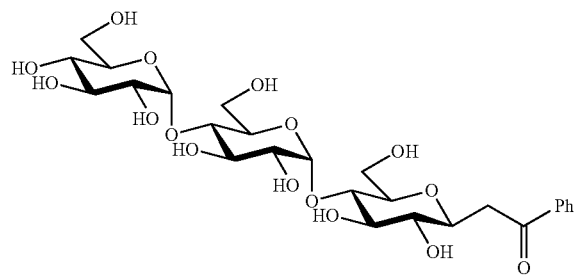
7cd
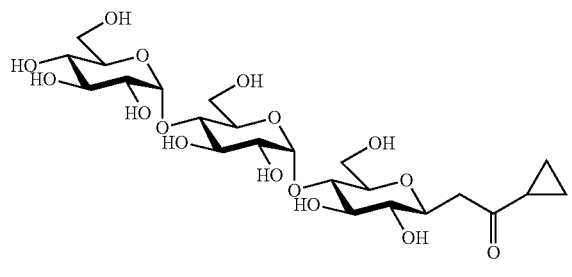
7cg
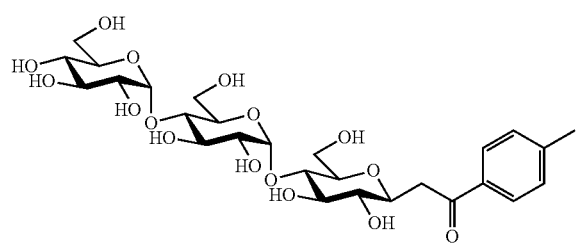
7ci
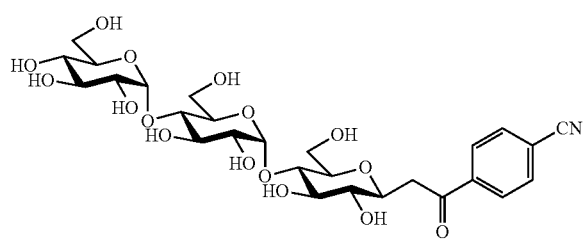
8a
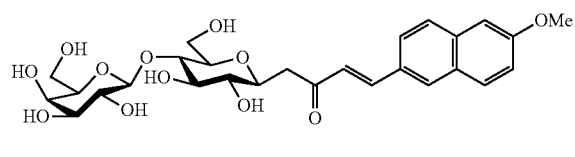
8b
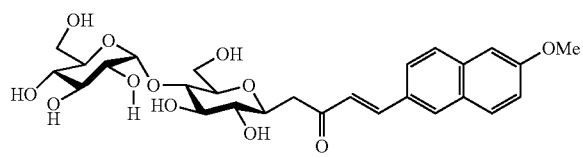
8c
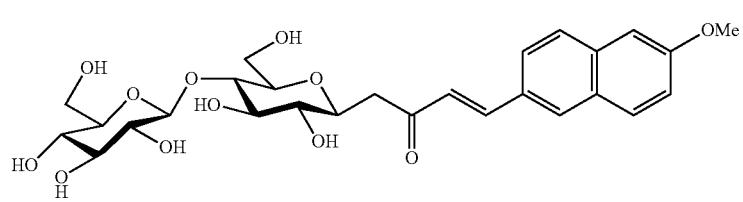
8d
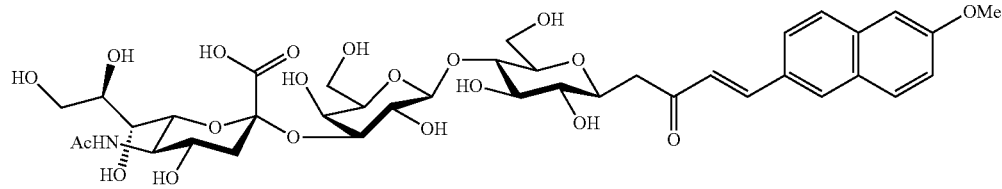
8e
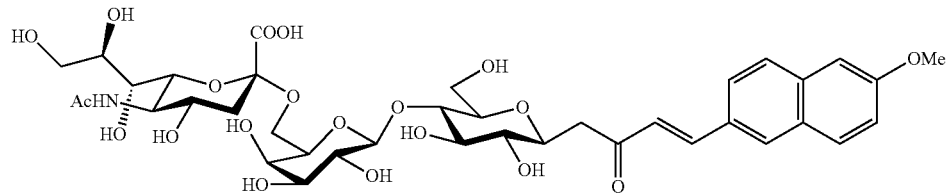
9
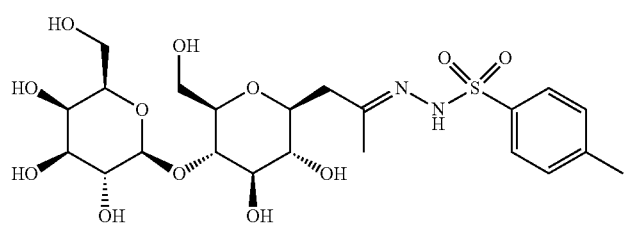

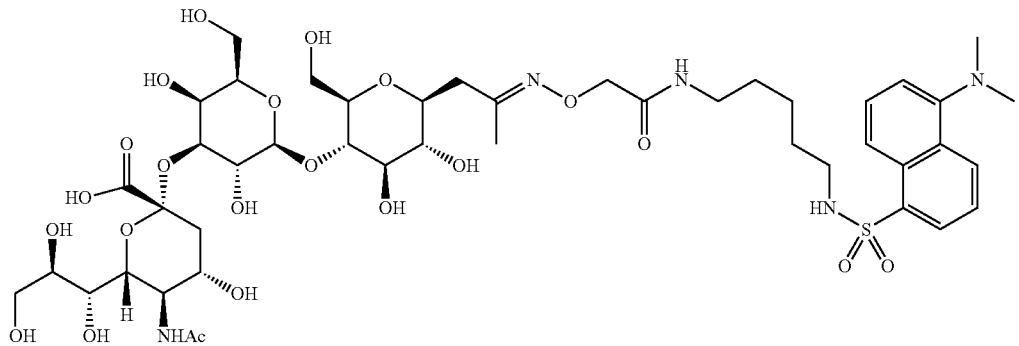

The present invention also provides a pharmaceutical composition, comprising the compound of formula I, I-1, I-1', or I-2, or a pharmaceutically acceptable salt thereof and a pharmaceutically acceptable carrier.

The "salt" of the compound may be any salt as long as the present invention can be carried out. The salt may be an acid-addition salt with an inorganic acid such as hydrochloric acid, hydrobromic acid, sulfuric acid, nitric acid, phosphoric acid, and the like, in particular hydrochloric acid, and with an organic acid such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine, and the like. In addition, the salt may be a salt which can be prepared by the reaction of the compound in a free acid form with an inorganic base or an organic base. Such salts prepared with inorganic bases include, but are not limited to, sodium salts, potassium salts, lithium salts, ammonium salts, calcium salts, magnesium salts, and the like. Salts prepared with organic bases include, but are not limited to, salts with primary, secondary, or tertiary amines, substituted amines, including naturally occurring substituted amines, cyclic amines, and basic ion exchange resins. Such salts may be salts with isopropylamine, trimethylamine, diethylamine, triethylamine, tripropylamine, ethanolamine, lysine, arginine, N-ethylpiperidine, piperidine, polyimine resins, and the like. When the salt is contained a pharmaceutical composition, a pharmaceutically acceptable salt is preferable.

The pharmaceutical composition can be formulated into a pharmaceutical preparation. The pharmaceutical preparation may be for oral administration, for example, in the form of tablets, coated tablets, dragees, hard or soft capsules, solutions, emulsions, or suspensions, or may be for rectal administration, for example, in the form of suppositories, or may be for parenteral administration, for example, in the form of injection solutions.

The pharmaceutical composition can contain a pharmaceutically acceptable carrier such as pharmaceutically acceptable inorganic or organic excipients suitable for the production of tablets, coated tablets, dragees, and soft or hard gelatin capsules.

Examples of the excipient suitable for the production of tablets, dragees, and hard gelatin capsules include, but are not limited to, lactose, corn starch or derivatives thereof, talc, stearic acid or its salts, and the like.

Examples of the excipient suitable for the production of soft gelatin capsules include, but are not limited to, vegetable oils, waxes, fats, semisolid polyols, liquid polyols, and the like.

Examples of the excipient suitable for the production of solutions and syrups include, but are not limited to, water, polyols, saccharose, invert sugar, glucose, and the like.

Examples of the excipient suitable for the production injection solutions include, but are not limited to, water, alcohols, polyols, glycerol, vegetable oils, and the like.

Examples of the excipient suitable for the production of suppositories include, but are not limited to, natural or hardened oils, waxes, fats, semiliquid polyols, liquid polyols, and the like.

Other than the excipient, the pharmaceutical composition can contain additive(s) that are generally used for manufacturing a medicament, where necessary. Examples of such additive include, but are not limited to, preservatives, solubilizers, stabilizers, wetting agents, emulsifiers, sweeteners, colorants, flavorants, salts for modifying the osmotic pressure, buffers, masking agents, and antioxidants.

If desired, the pharmaceutical composition may contain two or more pharmaceutically active ingredients.

The dosage may be varied according to sex, age, condition, and the like of the subject to be administered. In general, in the case of oral administration, a daily dosage of about 10 mg to about 1000 mg of the compound of formula I, I-1, I-1', or I-2 could be appropriate. The dosage can be administered in a single dose or a divided dose.

The present invention provides a novel process for preparing oligosaccharide C-glycoside derivatives that can be conducted under high stereoselective, mild, and atom-economical conditions, and by such process, novel oligosaccharide C-glycoside derivatives that could not be obtained by the previously known methods can be prepared. The present inventive process is step- and atom-economical (i.e., shorter reaction routes, less waste generation compared to the previously known methods). The present inventive compounds can be used as therapeutics, bioactives, bioactive candidates, probes, and the like, as well as their synthons and components. For example, glucose-bearing-carbohydrate-fluorescent molecule conjugates can be used for visualization of glucose-transporter-enriched cells. Glucose-bearing-carbohydrate-cancer drug conjugates can be used to deliver the conjugated drugs to cancer cells more efficiently. Sialyllactose-fluorescent molecule conjugates can be used for visualization of viruses. Depending on the carbohydrate structure, the molecules can provide antibacterial and/or antiviral activities. The present inventive process can be used for the conjugation or covalent attachment of oligosaccharides to surface of assay plate wells and to other molecules, which are used for diagnosis methods and/or as therapeutics and molecular probes used in diagnostics and in biomedical research.

Hereafter, the present invention will be explained in more detail.

C-Glycosides bearing ketone groups have been used for the synthesis of various C-glycoside derivatives. The inventors designed herein C-glycosidation of unactivated and unprotected di- and trisaccharide aldoses with ketones. In the inventors' design, the following points were considered to develop the C-glycosidation reactions: (1) in situ-activation of aldopyranoses to enable the C-C bond formation at the anomeric center, (2) in situ-generation of enamines or enolates from ketones that react as nucleophiles with aldopyranoses, (3) catalyst systems that work in the presence of polyhydroxy-substituted compounds, and (4) reaction systems/catalyst systems that provide high stereoselectivity for the C-C bond formation without altering the carbohydrate stereochemistry. The inventors sought amine-based catalysts to address these points and to enable the generation of desired products under mild conditions. In the inventors' design, amine catalysts were expected to form enamines of ketones. At the same time, the catalyst systems would activate the carbohydrates to lead the C-C bond formation. Based on these considerations, the inventors searched for catalysts of the C-glycosidation.

The inventors previously reported C-glycosidation of unprotected 2-N-acyl-aldopyranoses (Johnson, S.; Tanaka, F. Org. Biomol. Chem. 2016, 14, 259-264). In this reaction, some catalyst systems were efficient only for specific carbohydrates and the efficiency of the catalyst systems depended on the carbohydrate structure/stereochemistry.

For the C-glycosidation of di- and trisaccharide aldopyranoses with ketones, the inventors focused on the development of the catalyst systems that work for a series of carbohydrates, including functionalized carbohydrates, and for various ketones.

As described below, the catalyst systems composed of pyrrolidine and boric acid accelerated the C-glycosidation reactions of unprotected di- and trisaccharides with ketones.

C-Glycosidation of Monosaccharide Aldopyranoses

The inventors reasoned that catalyst systems that work for the C-glycosidation of di- and trisaccharide aldopyranoses with ketones should work for C-glycosidation of monosaccharide aldopyranoses to some degree. By analyzing the C-glycosidation products from monosaccharide aldopyranoses, features of the reactions, such as the possibility of isomerization at the 2-position of the carbohydrates, would be more easily recognized than by analyzing the products from di- and trisaccharides. Thus, first, the results of the C-glycosidation reactions of monosaccharide aldopyranoses are described. When the reaction was performed using pyrrolidine and boric acid as catalyst, C-glycoside ketone 3aa was obtained (Table 1).

For the reaction of D-glucose (1a) with acetone (2a), amine-based catalyst systems that have been commonly used in aldol and/or Mannich reactions of ketones with simple aldehydes (i.e., not carbohydrates), such as proline and amino acids, did not give 3aa. As 6-membered hemiacetals are usually stable as the cyclic forms, aldopyranoses, such as D-glucose, are more difficult to react with nucleophiles at the anomeric carbon (or the aldehyde carbonyl group of the corresponding ring-opened form) than are aldopentoses such as ribose. Conditions used for catalyzing the C-glycosidation of ribose with simple ketones, such as proline-DBU, were also not optimal for the C-glycosidation of D-glucose with acetone.

In the presence of pyrrolidine and boric acid, the reaction of D-glucose (1a) with ethyl 5-oxohexanoate (2b) also afforded C-glycoside product 3ab (Table 1). The ester group of ketone 2b was not affected under the pyrrolidine-boric acid catalysis conditions. Reaction with acetophenone (2c) also afforded the corresponding C-glycoside 3ac. The reactions of $C_6$-aldoses bearing 2-hydroxy group with acetophenone were previously recognized as difficult reactions (Wei, X.; Shi, S.; Xie, X.; Shimizu, Y.; Kanai, M. ACS Catal. 2016, 6, 6718-6722). The reaction of D-mannose (1b) with ketone 2b also afforded C-glycosidation product 3bb when the pyrrolidine-boric acid combination was used as a catalyst.

TABLE 1

C-Glycosidation of monosaccharide aldohexopyranoses.[a]

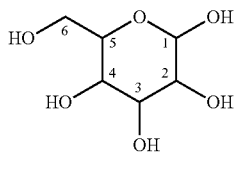

| 1 | product 3 | yield |
|---|---|---|
| 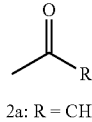<br>D-glucose (1a) | 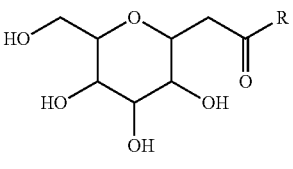<br>3aa | 25%[b]<br>12%[c] |

TABLE 1-continued

C-Glycosidation of monosaccharide aldohexopyranoses.[a]

| 1 | product 3 | yield |
|---|---|---|
| | 3ab | 37% |
| | 3ac | 17% |
| D-mannose (1b) | 3bb | 20% |

[a]Conditions: Carbohydrate 1 (0.50 mmol), ketone 2 (2.0 mmol), pyrrolidine (0.25 mmol), $H_3BO_3$ (1.0 mmol) in DMSO (1.0 mL) at room temperature (25° C.) for 48 h.
[b]Acetone (5.0 mmol).
[c]Acetone (20 equiv to 1a), boric acid (1.0 equiv to 1a), 24 h; modified conditions; see the Examples.

Under the pyrrolidine-boric acid catalysis conditions, isomerization at the 2-position of the carbohydrates did not occur: The reaction of D-glucose affording 3ab did not co-generate 3bb, and the reaction of D-mannose affording 3bb did not form 3ab.

Isolated products 3 were stable at room temperature (25° C.) for at least one month. Acetal formation at the ketone group of these products and the formation of ring-opened forms were negligible or were not detected.

Previously reported C-glycosidation reactions of $C_6$-aldoses with ketones (excluding 1,3-diketones and relatively nucleophilic ketones) were often performed with aldoses that did not have a hydroxy group at the 2-position of the aldoses. The pyrrolidine-boric acid catalyst system allowed the synthesis of C-glycoside derivatives of $C_6$-aldopyranoses bearing a hydroxy group at the 2-position. Further, in the reactions catalyzed by the pyrrolidine-boric acid system, products were obtained as single diastereomers or with high diastereoselectivity with the β-isomer as the major diastereomer (dr (β-anomer/α-anomer)>10:1 to >20:1).

Until the present invention, C-glycoside products bearing ketone moieties were synthesized by the reactions of unprotected carbohydrates with β-diketones (Richter, C.; Krumrey, M.; Bahri, M.; Trunschke, S.; Mahrwald, R. ACS Catal. 2016, 6, 5549-5552) or with Horner-Wadsworth-Emmons (HWE) β-carbonyl phosphonate reagents (Ranoux, A.; Lemiegre, L.; benoit, M.; Guegan, J.-P.; Benvegnu, T. Eur. J. Org. Chem. 2010, 1314-1323). These reactions were performed at high temperature under basic conditions. The reactions of unprotected carbohydrates with ketones using pyrrolidine-boric acid catalyst afforded the products under mild conditions at room temperature. With the use of pyrrolidine-boric acid catalysis system, methyl ketone derivatives with the ester group and with the aryl group were able to be used as nucleophiles, and the synthesis of β-diketones and of HWE reagents was not required to obtain the C-glycoside products.

C-Glycosidation of Disaccharide Aldopyranoses
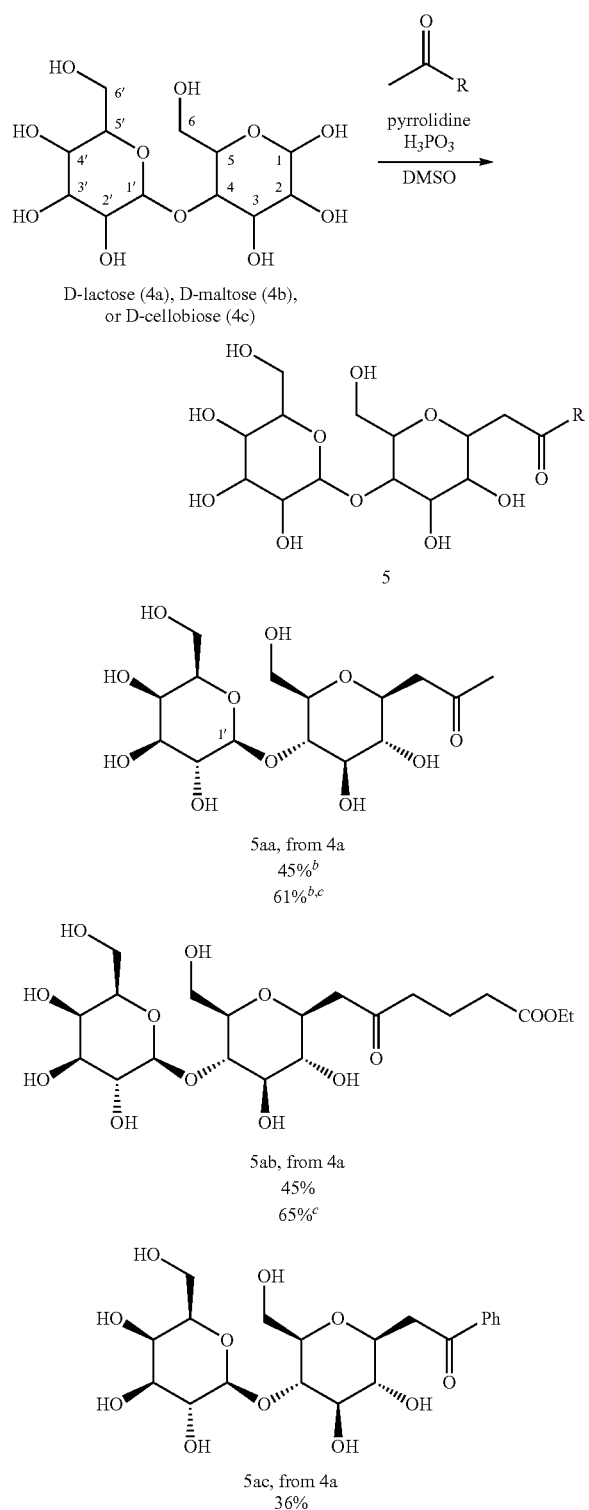
Scheme 1 C-Glycosidiation of disaccharides.[a]
[Chem.35]
D-lactose (4a), D-maltose (4b), or D-cellobiose (4c)
5aa, from 4a
45%[b]
61%[b,c]
5ab, from 4a
45%
65%[c]
5ac, from 4a
36%
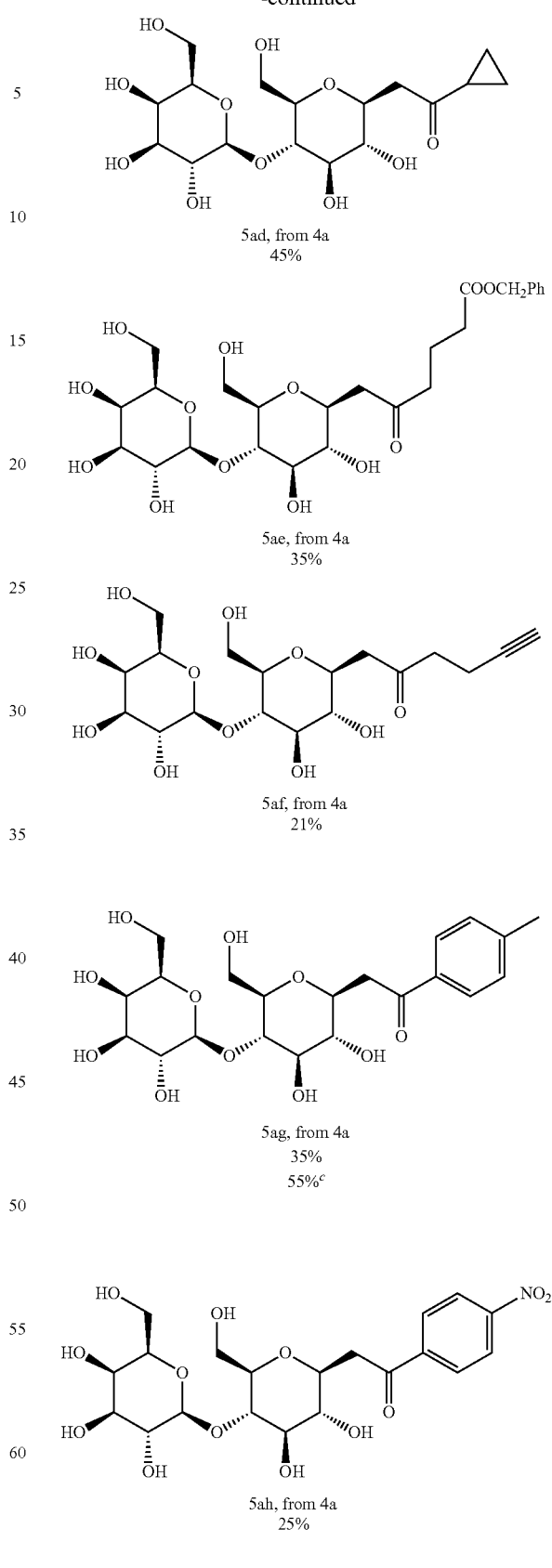
5ad, from 4a
45%
5ae, from 4a
35%
5af, from 4a
21%
5ag, from 4a
35%
55%[c]
5ah, from 4a
25%

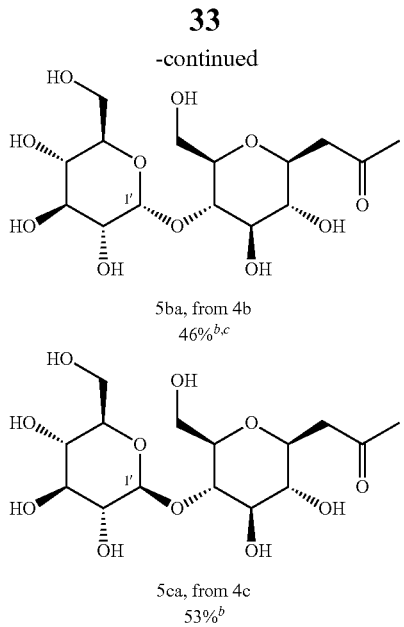

5ba, from 4b
46%[b,c]

5ca, from 4c
53%[b]

[a]Conditions: Carbohydrate4 (0.5 mmol, 1.0 equiv), ketone 2 (2.0 mmol, 4.0 equiv), pyrrolidine (0.25 mmol, 0.5 equiv), H$_3$BO$_3$ (1.0 mmol, 2.0 equiv) in DMSO (1.0 mL at room temperature (25° C.) for 48 h.
[b]Modified conditions with 4 (1.0 equiv), acetone (20 equiv), pyrrolidine (0.5 equiv), and H$_3$BO$_3$ (1.0 equiv); see the Examples.
[c]96 h.

[a] Conditions: Carbohydrate 4 (0.5 mmol, 1.0 equiv), ketone 2 (2.0 mmol, 4.0 equiv), pyrrolidine (0.25 mmol, 0.5 equiv), H$_3$BO$_3$ (1.0 mmol, 2.0 equiv) in DMSO (1.0 mL) at room temperature (25° C.) for 48 h. [b] Modified conditions with 4 (1.0 equiv), acetone (20 equiv), pyrrolidine (0.5 equiv), and H$_3$BO$_3$ (1.0 equiv); see the Examples. [c] 96 h.

C-Glycosidation reactions of disaccharide aldopyranoses 4 are shown in Scheme 1. Under the pyrrolidine-boric acid catalysis conditions, reactions of D-lactose (4a) with ketones afforded the corresponding C-glycosidation products 5aa-5ah (Scheme 1). These products were β-isomers (dr ((β/α)>10:1) regardless of the reaction time lengths. Reactions with various ketones, such as acetone, unsymmetrical functionalized alkyl methyl ketones (including ketones bearing an ester group, an ethynyl group, or a cyclopropane ring), and aryl methyl ketones, afforded the desired C-glycosidation products.

When amine-based catalyst systems were screened to afford 5aa in the reaction of D-lactose (1a) with acetone, commonly used amine-based catalysts such as proline did not catalyze the reaction. Proline with bases such as N,N-diisopropylethylamine also did not efficiently catalyze the reaction. Among catalyst systems tested, pyrrolidine-boric acid most efficiently catalyzed the reaction. Investigation of catalyst systems for the reaction of 4a is further discussed in the later part (see below).

Under the pyrrolidine-boric acid catalysis conditions, reactions of D-maltose (4b) and of D-cellobiose (4c) also afforded the corresponding C-glycosides 5ba and 5ca, respectively (Scheme 1). Products 5ba and 5ca were also obtained as β-isomers (dr (β/α)>10:1).

The pyrrolidine-boric acid catalysis conditions did not affect the stereochemistry of the O-glycosylated carbon of the disaccharide (i.e., the 1'-position of the disaccharides) (Scheme 1). In the reaction of D-maltose (4b) affording 5ba, the formation of 5ca was not observed, and in the reaction of D-cellobiose (4c) affording 5ca, the formation of 5ba was not detected. For products 5 obtained from D-lactose, in the $^1$H NMR spectra, the coupling constant J value of the proton at the 1'-position indicated that the stereochemistry of the 1'-position of the reactant was retained in the products.

Reactions of disaccharides 4a, 4b, and 4c were faster than reactions of monosaccharides 1 under the same pyrrolidine-boric acid catalysis conditions when the reactions with the same ketones were compared. The yields of the disaccharide C-glycoside derivatives after 48 h were better than those of monosaccharide C-glycoside derivatives when the same ketones were used under the same reaction conditions (Scheme 1, 5ab versus Table 1, 3ab and 3bb; Scheme 1, 5ac versus Table 1, 3ac). Yields of products 5 were improved with longer reaction time without increased formation of by-products (Scheme 1, for 5aa: 45% after 48 h, 61% after 96 h; for 5ab: 45% after 48 h, 65% after 96 h; for 5ag: 35% after 48 h, 55% after 96 h).

In contrast, for D-melibiose (4d) in which the hydroxy group at the 6-position of the terminal aldopyranose is glycosylated, the corresponding C-glycosidation products were not formed under the pyrrolidine-boric acid catalysis conditions.

[Chem.36]

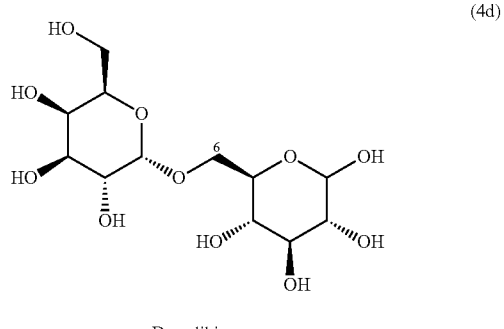

(4d)

D-melibiose

C-Glycosidation of Trisaccharide Aldopyranoses

Scheme 2 C-Glycosidiation of trisaccharides.[a]

[Chem.37]

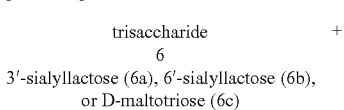

trisaccharide       +
6
3'-sialyllactose (6a), 6'-sialyllactose (6b), or D-maltotriose (6c)

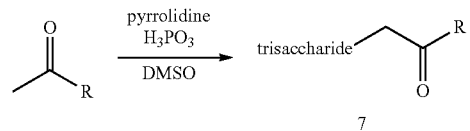

7

35
-continued

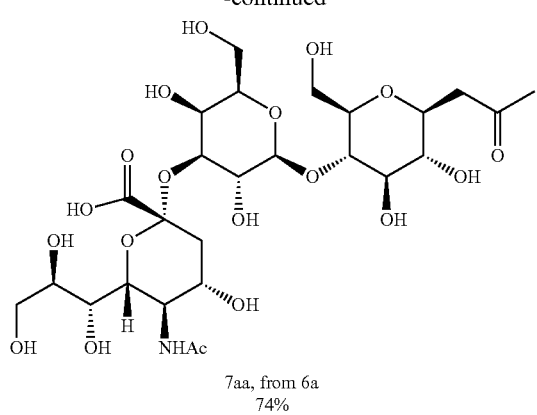

7aa, from 6a
74%

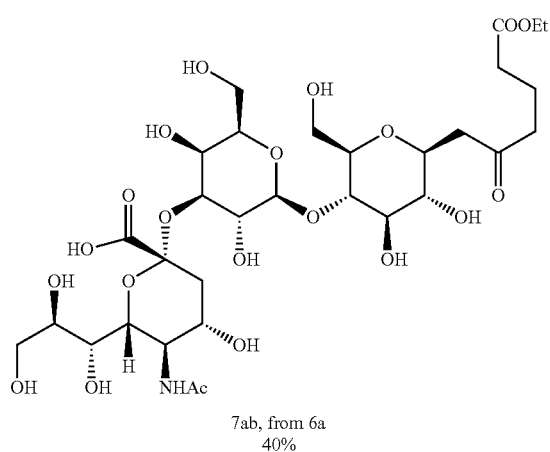

7ab, from 6a
40%

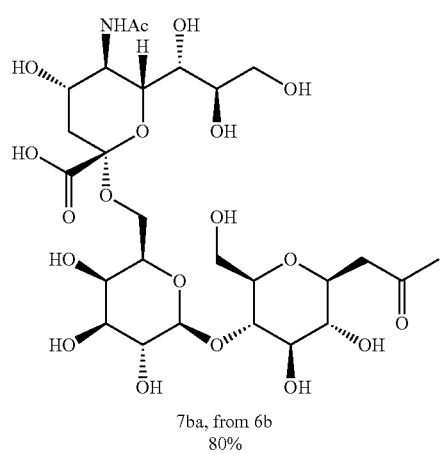

7ba, from 6b
80%

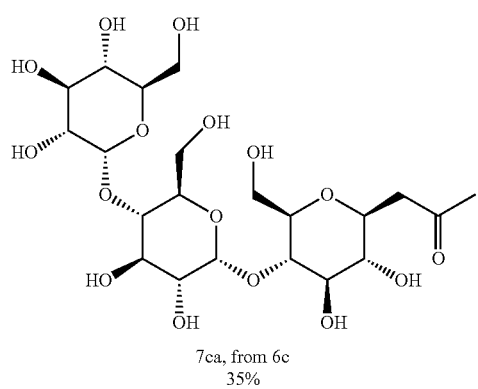

7ca, from 6c
35%

36
-continued

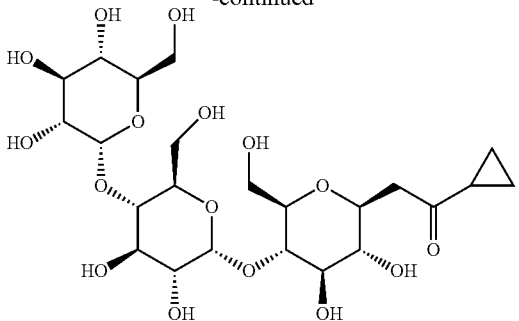

7cd, from 6c
30%

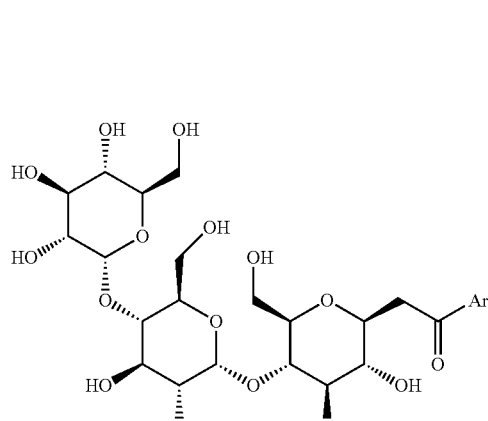

7cc: Ar = Ph
from 6c
22%
7cg: Ar = C$_6$H$_4$-p-Me
from 5c
25%
7ci: Ar = C$_6$H$_4$-p-CN
from 6c
22%

[a]For details, see the Examples.

Reactions of trisaccharide aldopyranoses 6 were also performed using pyrrolidine-boric acid catalysis conditions. With the use of the pyrrolidine-boric acid catalyst system, reactions of 3'-sialyllactose (6a), 6'-sialyllactose (6b), and maltotriose (6c) with ketones afforded the corresponding C-glycosides 7 (Scheme 2). Reactions with acetone, alkyl methyl ketones bearing various functional group or a cyclopropane ring, and aryl methyl ketones all gave the desired C-glycoside ketones 7. Use of the pyrrolidine-boric acid catalyst system allowed the direct C-glycosidation reactions of highly functionalized carbohydrates such as N-acetylneuraminic acid-bearing carbohydrates.

Transformations of C-Glycoside Ketones
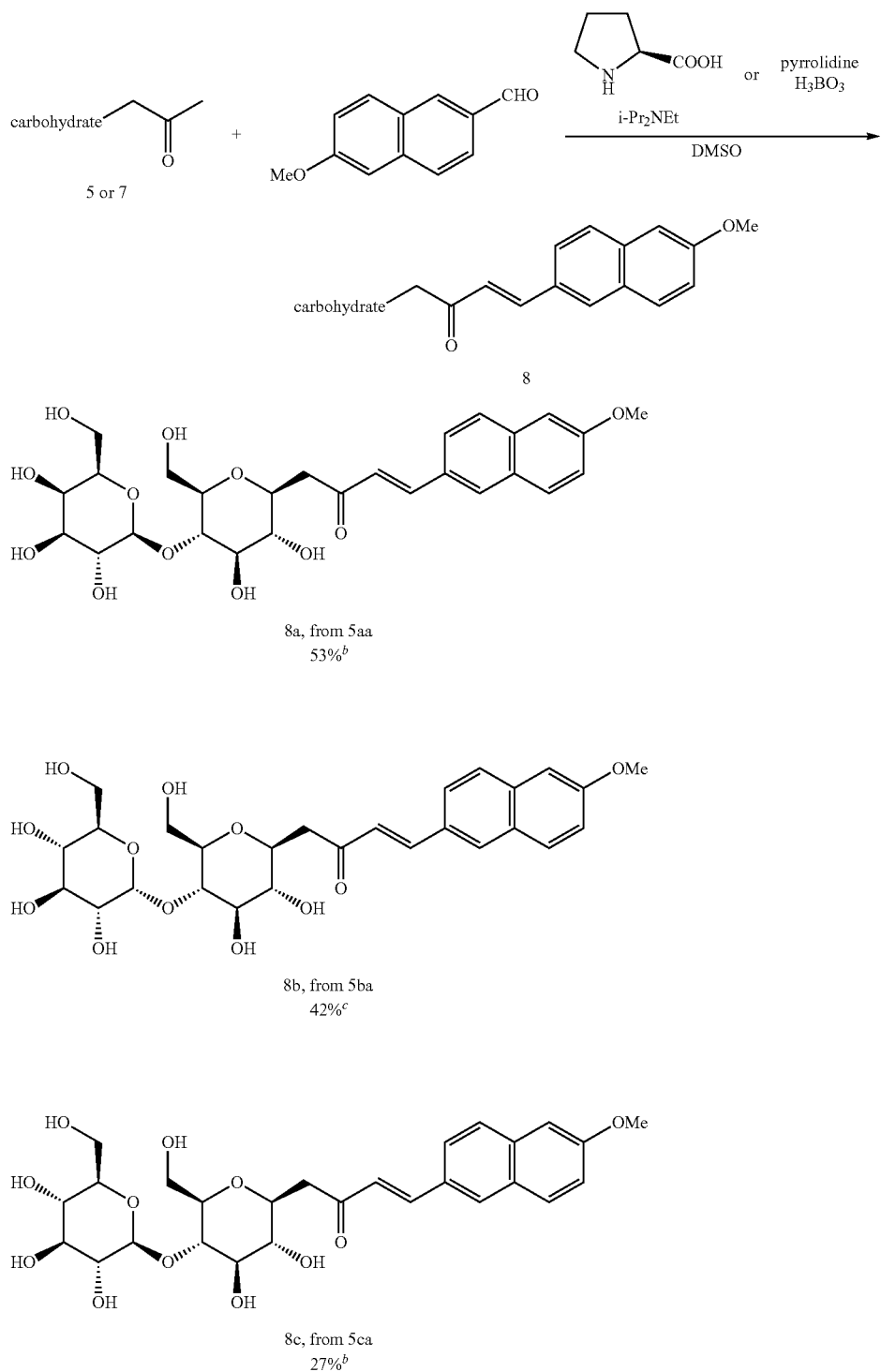
Scheme 3 Transformations of C-glycoside ketones through aldol condensation.[a]
[Chem.38]
8a, from 5aa
53%[b]
8b, from 5ba
42%[c]
8c, from 5ca
27%[b]

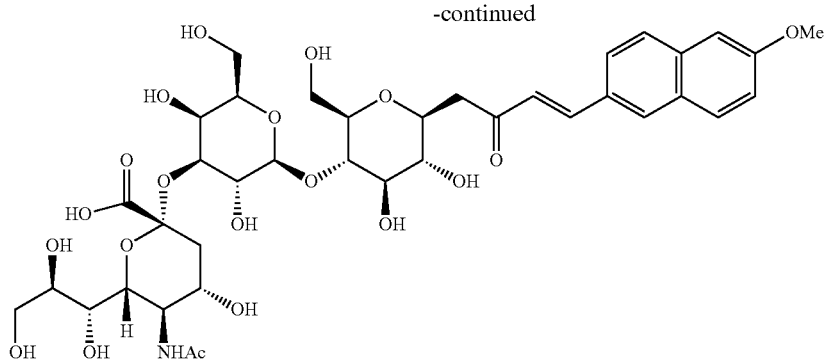
8d from 7aa
40%[c]
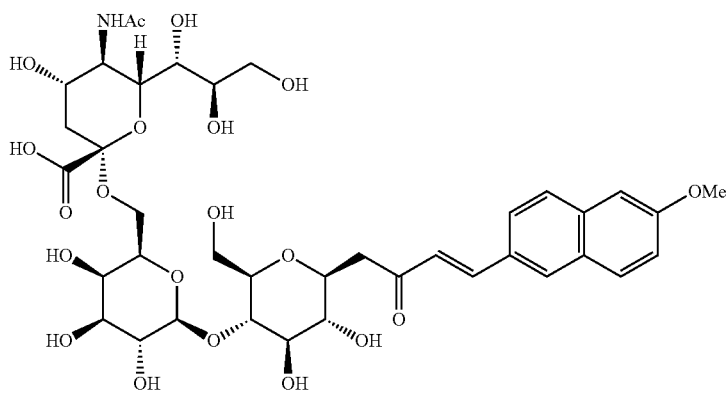
8e from 7ba
35%[c]
[a]For details, see the Examples. [b]Proline-i-Pr₂NEt catalysis. [c]Pyrrolidine-boric acid catalysis.
Scheme 4 Derivatization through hydrazone formation.
[Chem.39]
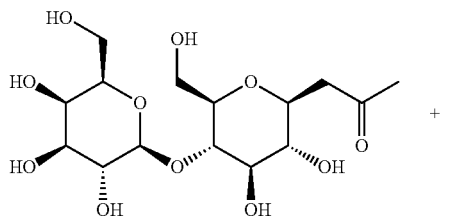
5aa
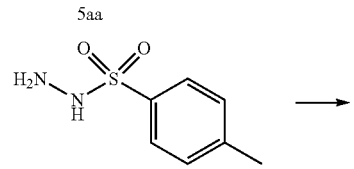
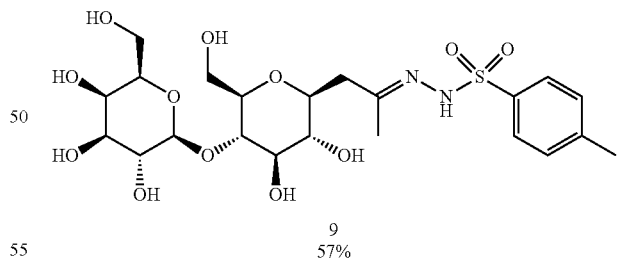
9
57%
Scheme 5 Derivatization through oxime formation followed by amide formation.

[Chem.40]

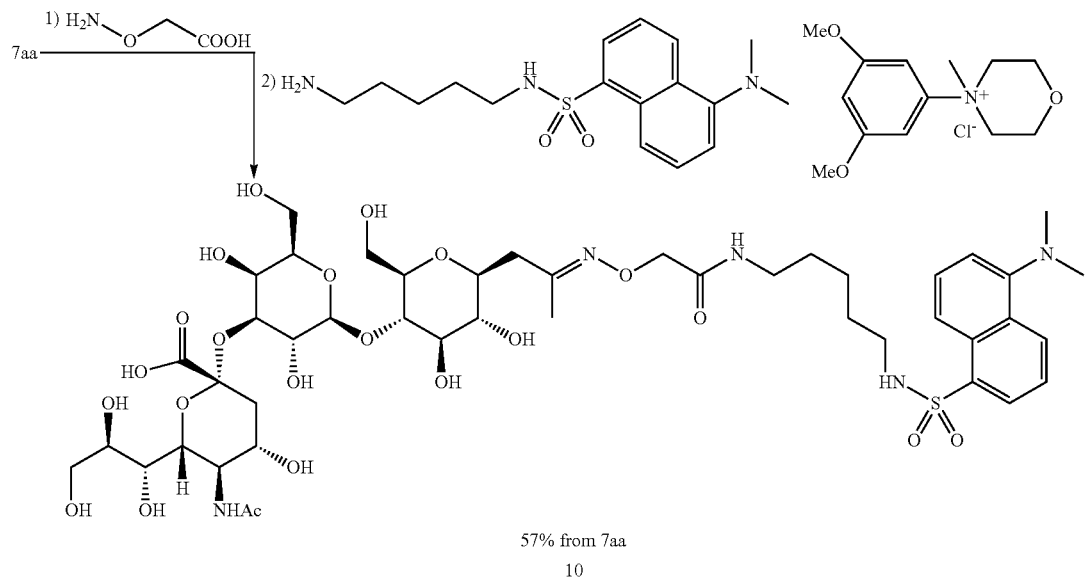

57% from 7aa
10

The methyl ketone moiety of monosaccharide C-glycoside ketones and of a few disaccharide C-glycosides has been used as a reaction site for chemical transformations to derivatize the C-glycoside ketones. The C-glycoside ketones synthesized using the pyrrolidine-boric acid catalysis conditions were transformed to C-glycoside derivatives with more complex and/or elongated structures (Schemes 3, 4, and 5). The methyl ketone moiety was used as a nucleophile (via the formation of enamines or enolates) to generate aldol condensation products 8 (Scheme 3). The methyl ketone moiety was also used as an electrophile to form hydrazone derivative 9 and oxime derivative 10 (Schemes 4 and 5).

Carbohydrate derivatives bearing a 6-methoxynaphthalen-2-yl-buten-2-one moiety are inhibitors of certain cancer-associated enzymes. Until the present invention, monosaccharide C-glycoside ketones have been derivatized to afford aldol condensation products. In the present invention, di- and trisaccharide C-glycosides were transformed to the corresponding aldol condensation products 8a-e using either proline-N,N-diisopropylethylamine or pyrrolidine-boric acid catalysis systems (Scheme 3). No protection of the polyhydroxy groups of the C-glycosides was necessary before the transformation. Through the formation of 8, the formation of 5 and 7 in the C-glycosidation reactions was further confirmed.

The C-glycosidation using the pyrrolidine-boric acid catalysis allowed the synthesis of C-glycoside ketones bearing functional groups (such as ethynyl, ester, and aryl ketone groups) as described above. These functional groups will also be useful for further derivatization.

Catalyst Systems in the C-Glycosidation

To understand the key factors that result in the generation of the C-glycosides from di- and trisaccharide aldopyranoses using pyrrolidine-boric acid catalysis system, related catalyst systems were also evaluated in the reaction of D-lactose (4a) with ketone 2b to afford 5ab and with ketone 2c to afford 5ac (Table 2).

TABLE 2

Catalyst systems for the C-glycosidation of 4a.[a]

2b, 5ab: R = (CH$_2$)$_3$COOEt
2c, 5ac: R = Ph

| entry | catalyst system | product | yield (%) |
|---|---|---|---|
| 1 | pyrrolidine-H$_3$BO$_3$ | 5ab | 45[b] |
| 2 | pyrrolidine-B(OMe)$_3$ | 5ab | 39 |
| 3 | pyrrolidine-NaOH | 5ab | —[c] |
| 4 | pyrrolidine-Na$_2$CO$_3$ | 5ab | —[c] |
| 5 | pyrrolidine-DBU | 5ab | <5 |
| 6 | pyrrolidine-NH$_4$Cl | 5ab | —[c] |
| 7 | pyrrolidine-phenol | 5ab | <5 |
| 8 | pyrroldiine-CH$_3$COOH | 5ab | <5 |
| 9 | Et$_3$N—H$_3$BO$_3$ | 5ab | —[c] |
| 10 | DBU-H$_3$BO$_3$ | 5ab | —[c] |

TABLE 2-continued

Catalyst systems for the C-glycosidation of 4a.[a]

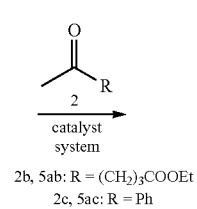

2b, 5ab: R = (CH$_2$)$_3$COOEt
2c, 5ac: R = Ph

| entry | catalyst system | product | yield (%) |
|---|---|---|---|
| 11 | pyrrolidine | 5ab | —[c] |
| 12 | H$_3$BO$_3$ | 5ab | —[c] |
| 13 | pyrrolidine-H$_3$BO$_3$ | 5ac | 36[b] |
| 14 | PhCH$_2$NH$_2$—H$_3$BO$_3$ | 5ac | 30 |

[a]Conditions: For entry 2, carbohydrate 4a (0.25 mmol), ketone 2b or 2c (2.0 mmol), pyrrolidine (0.13 mmol), B(OMe)$_3$ (0.5 mmol) in DMSO (0.5 mL) at room temperature (25° C.) for 48 h. For entries 3-12 and 14, H$_3$BO$_3$ and/or pyrrolidine were subtracted or replaced as indicated.
[b]Data from Scheme 1.
[c]Formation of 5ab was not detected.

Pyrrolidine alone or boric acid alone did not catalyze the reaction to form the C-glycosidation product; carbohydrate 4a remained unreacted (entries 11 and 12). Substituting boric acid with bases, such as NaOH, Na$_2$CO$_3$, or DSU, in the catalyst system also did not afford 5ab (entries 3-5). Substituting boric acid with NH$_4$Cl, phenol, or acetic acid also did not form the product (entries 6-8). On the other hand, the pyrrolidine-trimethyl borate catalyst system catalyzed the reaction to afford product 5ab (entry 2). These results suggest that boric acid in the pyrrolidine-boric acid catalysis in the C-glycosidation acts not just as a Broensted acid or base. It is likely that boric acid forms B—O covalent bonds with the carbohydrate. This B—O covalent formation may be key to the formation of the C-glycosidation product (see below).

Further, the use of Et$_3$N or DBU instead of pyrrolidine in the pyrrolidine-boric acid catalysis system did not catalyze the reaction to give the C-glycosidation product (entries 9 and 10). Although DBU has been used to generate enolates from ketones, the DBU-boric acid system was not effective for the C-glycosidation with ketones. However, substituting pyrrolidine with benzylamine in the pyrrolidine-boric acid catalysis system did afford C-glycosidation product 5ac (entry 14). Benzylamine has been used as an amine component in enamine-forming catalyst systems (Cui, H.-L.; Chouthaiwale, P. V.; Yin, F.; Tanaka, F. Asian J. Org. Chem. 2016, 5, 153-161). These results indicated that both pyrrolidine (or amine, which can form an imine/iminium ion/enamine) and boric acid (or borate) have functions for catalyzing the C-glycosidation reaction. These results suggest that the pyrrolidine-boric acid catalyst system involves both the formation of an iminium ion with the carbohydrate and the formation of an enamine of the ketones during the catalysis.

The present invented C-glycosidation reaction methods that use the pyrrolidine-boric acid catalyst system allow access to di- and trisaccharide-derived C-glycosides derivatives including those that were previously difficult to synthesize. Insights obtained from our investigation on the mechanisms of the pyrrolidine-boric acid catalysis for the C-glycosidation will be useful for the development of related catalyzed reactions.

It is to be understood that as used herein and in the claims, the singular forms "a," "an," and "the" should generally be construed to mean "one or more" and include plural reference unless the context clearly dictates otherwise.

It is also to be understood that the scope of the invention should not be limited to the particular forms disclosed herein and the invention covers all modifications, equivalents, and alternatives falling within the spirit and scope of the invention as defined by the claims.

EXAMPLES

The following examples further illustrate the present invention but, of course, should not be construed as limiting the scope of the invention in any way.

1. C-Glycosidation of Monosaccharide Aldopyranoses (Table 1)

General Procedure for the Synthesis of C-glycosides 3

A mixture of carbohydrate (0.50 mmol, 1.0 equiv) and ketone (2.0 mmol, 4.0 equiv) in DMSO (1.0 mL) was stirred at room temperature (25° C.) for 5 min to solubilize the carbohydrate. To the solution, pyrrolidine (0.25 mmol, 0.5 equiv) and boric acid (1.0 mmol, 2.0 equiv) were added and the mixture was stirred at the same temperature for 48 h. The mixture was purified by silica gel flash column chromatography (CH$_2$Cl$_2$/MeOH or CHCl$_3$/MeOH) to give the corresponding C-glycoside 3.

In our observation, after 48 h reaction time, starting material carbohydrate 1 remained significantly, and thus the moderate yields of 3 were obtained. The corresponding hemiketal forms were possibly generated as a portion during the reactions depending on reaction conditions and also depending on carbohydrates and ketones used in the reactions, although they were not isolated or confirmed.

Compound 3aa was synthesized by the general procedure from D-glucose (90 mg, 0.50 mmol) but using 10 equiv of acetone (368 μL, 5.0 mmol), and purified by flash column chromatography (CHCl$_3$/MeOH=88:12 to 85:15), colorless gum, 27 mg, 25%. Compound 3aa is a known compound.
$R_f$=0.37 (CH$_2$Cl$_2$/MeOH=5:1). $^1$H NMR (400 MHz, CD$_3$OD): δ 3.78 (dd, J=12.0 Hz, 1.7 Hz, 1H), 3.66 (td, J=9.2 Hz, 2.9 Hz, 1H), 3.61 (dd, J=12.0 Hz, 5.0 Hz, 1H), 3.36-3.29 (m, 1H), 3.28-3.20 (m, 2H), 3.06 (t, J=9.2 Hz, 1H), 2.88 (dd, J=16.0 Hz, 2.9 Hz, 1H), 2.59 (dd, J=16.0 Hz, 9.2 Hz, 1H), 2.20 (s, 3H). $^{13}$C NMR (100 MHz, CD$_3$OD): δ 210.2, 81.6, 79.6, 77.2, 75.1, 71.7, 62.8, 47.1, 30.6. HRMS (ESI): calcd for C$_9$H$_{17}$O$_6$ ([M+H]$^+$) 221.1020, found 221.1023.

Compound 3aa was also synthesized using pyrolidine (0.5 equiv) and boric acid (1.0 equiv). To a mixture of pyrrolidine (28.0 μL, 0.34 mmol) in DMSO (1.0 mL), acetone (1.0 mL, 13.6 mmol) and boric acid (42.0 mg, 0.68 mmol) were added at room temperature (25° C.), and the mixture was stirred for 5 min. To this mixture, glucose (150 mg, 0.68 mmol) was added and the mixture was stirred at the same temperature for 24 h. The mixture was purified by silica gel flash column chromatography (CH$_2$Cl$_2$/MeOH=86:14 to 78:22) to give 3aa (19.1 mg, 12%) with the 5-membered ring isomers and the further cyclized forms through hemiketal formation.

Compound 3aa was also synthesized using using L-proline and triethylamine. To a mixture of L-proline (192 mg, 1.67 mmol) in PEG (5.0 mL), acetone (4.90 mL, 66.6 mmol) and triethylamine (116 μL, 0.833 mmol) were added at room temperature (25° C.), and the mixture was stirred for 5 min. To this mixture, glucose (600 mg, 3.33 mmol) was added and the mixture was stirred at the same temperature for 24 h. The mixture was purified by silica gel flash column chromatography (CH$_2$Cl$_2$/MeOH=86:14 to 78:22) to give a mixture of product including 3aa with the 5-membered ring isomers and further cyclized forms through hemiketal formation (93.0 mg, 88%). Based on further purification by silica gel flash column chromatography (CH$_2$Cl$_2$/MeOH=86:14 to 78:22) and $^1$H NMR analyses of fractions containing 3aa, the yield of 3aa was estimated to be 18%.

Compound 3ab was synthesized by the general procedure from D-glucose (90 mg, 0.50 mmol) and ethyl 5-oxohexanoate (320 μL, 2.0 mmol), and purified by flash column chromatography (CH$_2$Cl$_2$/MeOH=88:12 to 80:20), pale yellow gum, 59 mg, 37%.
Rf=0.25 (CH$_2$Cl$_2$/MeOH=5:1). $^1$H NMR (400 MHz, CD$_3$OD): δ 4.08 (q, J=7.2 Hz, 2H), 3.75 (dd, J=11.9 Hz, 2.2 Hz, 1H), 3.63 (td, J=9.2 Hz, 2.8 Hz, 1H), 3.59 (dd, J=11.9 Hz, 5.8 Hz, 1H), 3.33-3.28 (m, 1H), 3.25 (dd, J=9.2 Hz, 9.0 Hz, 1H), 3.21-3.16 (m, 1H), 3.04 (t, J=9.2 Hz, 1H), 2.81 (dd, J=15.6 Hz, 2.8 Hz, 1H), 2.60-2.52 (m, 3H), 2.30 (t, J=7.2 Hz, 2H), 1.81 (quint, J=7.2 Hz, 2H), 1.21 (t, J=7.2 Hz, 3H). $^{13}$C NMR (100 MHz, CD$_3$OD): δ 211.1, 175.1, 81.6, 79.6, 77.3, 75.1, 71.6, 62.7, 61.4, 46.4, 43.0, 34.0, 19.7, 14.5. HRMS (ESI): calcd for C$_{14}$H$_{25}$O$_8$ ([M+H]$^+$) 321.1544, found 321.1543.

Compound 3ac was synthesized the general procedure from D-glucose (90 mg, 0.50 mmol) and acetophenone (233 μL, 2.0 mmol), and purified by flash column chromatography (CH$_2$Cl$_2$/MeOH=86:14 to 80:20), pale yellow gum, 24 mg, 17%. Compound 3ac is a known compound.
Rf=0.29 (CH$_2$Cl$_2$/MeOH=5:1). $^1$H NMR (400 MHz, CD$_3$OD): δ 8.01-7.99 (m, 2H), 7.60 (tt, J=7.4 Hz, 1.2 Hz, 1H), 7.52-7.47 (m, 2H), 3.86 (td, J=9.0 Hz, 2.5 Hz, 1H), 3.74 (dd, J=11.9 Hz, 2.4 Hz, 1H), 3.61 (dd, J=11.9 Hz, 5.0 Hz, 1H), 3.42 (dd, J=16.4 Hz, 2.5 Hz, 1H), 3.41-3.30 (m, 2H), 3.25-3.17 (m, 3H). $^{13}$C NMR (100 MHz, CD$_3$OD): δ 200.6, 138.5, 134.3, 129.7, 129.3, 81.5, 79.7, 77.3, 75.1, 71.6, 62.7, 42.4. HRMS (ESI): calcd for C$_{14}$H$_{19}$O$_6$ ([M+H]$^+$) 283.1176, found 283.1176.

Compound 3bb was synthesized the general procedure from D-mannose (90 mg, 0.50 mmol) and ethyl 5-oxohexanoate (320 μL, 2.0 mmol), and purified by flash column chromatography (CH$_2$Cl$_2$/MeOH=88:12 to 80:20), pale yellow gum, 32 mg, 20%.
Rf=0.27 (CH$_2$Cl$_2$/MeOH=5:1). $^1$H NMR (400 MHz, CD$_3$OD): δ 4.11 (q, J=7.2 Hz, 2H), 3.92 (ddd, J=7.6 Hz, 5.3 Hz, 0.9 Hz, 1H), 3.80 (dd, J=11.8 Hz, 2.4 Hz, 1H), 3.72 (dd, J=3.2 Hz, 0.8 Hz, 1H), 3.65 (dd, J=11.8 Hz, 5.6 Hz, 1H), 3.54 (t, J=9.4 Hz, 1H), 3.48 (dd, J=9.4 Hz, 3.2 Hz, 1H), 3.18 (ddd, J=9.4 Hz, 5.6 Hz, 2.4 Hz, 1H), 2.87 (dd, J=16.6 Hz, 7.6 Hz, 1H), 2.65 (dd, J=16.6 Hz, 5.3 Hz, 1H), 2.58 (t, J=7.2 Hz, 2H), 2.33 (t, J=7.2 Hz, 2H), 1.84 (quint, J=7.2 Hz, 2H), 1.24 (t, J=7.2 Hz, 3H). $^{13}$C NMR (100 MHz, CD$_3$OD): δ 210.5, 175.1, 82.0, 76.3, 75.7, 72.4, 68.5, 62.9, 61.4, 44.9, 42.9, 34.1, 19.8, 14.5. HRMS (ESI): calcd for C$_{14}$H$_{24}$O$_8$Na ([M+Na]$^+$) 343.1363, found 343.1364.

[Chem.41]

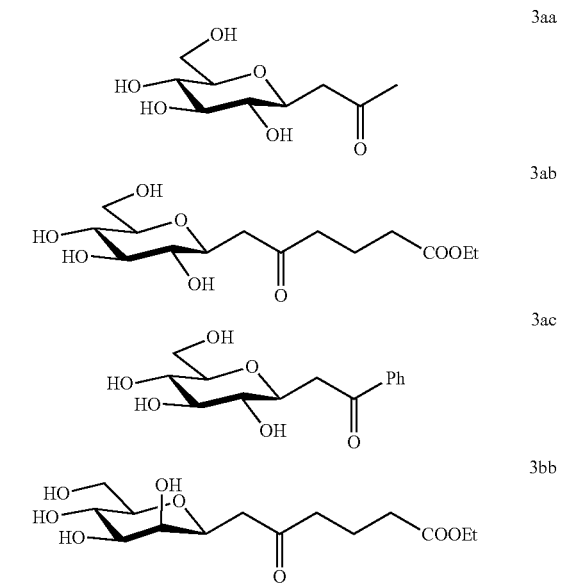

2. C-Glycosidation of Di- and Trisaccharide Aldopyranoses (Schemes 1 and 2)

Procedures for the Synthesis of C-glycosides 5 and 7

Procedure A

To a solution of pyrrolidine (0.15 mmol, 0.5 equiv) in DMSO (1.0 mL), acetone (5.8 mmol, 20 equiv) and boric acid (0.29 mmol, 1.0 equiv) were added at room temperature (25° C.) and the mixture was stirred for 5 min. To this mixture, carbohydrate (0.28-0.29 mmol, 1.0 equiv) was added and the mixture was stirred at the same temperature for 24 h. The mixture was purified by silica gel flash column chromatography (CH$_2$Cl$_2$/MeOH) to give the corresponding C-glycoside 5 or 7.

Procedure B

To a solution of pyrrolidine (0.15 mmol, 0.5 equiv) in DMSO (0.35 mL), acetone (5.8 mmol, 20 equiv) and boric acid (0.29 mmol, 1.0 equiv) were added at room temperature (25° C.) and the mixture was stirred for 5 min. To this mixture, carbohydrate (0.28-0.29 mmol, 1.0 equiv) was added and the mixture was stirred at the same temperature for 96 h. The mixture was purified by silica gel flash column chromatography (CH$_2$Cl$_2$/MeOH) to give the corresponding C-glycoside 5 or 7.

Procedure C

A mixture of carbohydrate (0.50 mmol, 1.0 equiv) and ketone (2.0 mmol, 4.0 equiv) in DMSO (1.0 mL) was stirred at room temperature (25° C.) for 5 min to solubilize the carbohydrate. To the solution, pyrrolidine (0.25 mmol, 0.5 equiv) and boric acid (1.0 mmol, 2.0 equiv) were added and the mixture was stirred at the same temperature for 48 h. The mixture was purified by silica gel flash column chromatography (CH$_2$Cl$_2$/MeOH) to give the corresponding C-glycoside 5 or 7.

Compound 5aa was synthesized by procedure A from D-lactose and acetone. To a solution of pyrrolidine (12.0 µL, 0.146 mmol) in DMSO (1.0 mL), acetone (429 µL, 5.84 mmol) and boric acid (18.0 mg, 0.292 mmol) were added at room temperature (25° C.) and the mixture was stirred for 5 min. To this mixture, D-lactose monohydrate (100 mg, 0.278 mmol) was added and the mixture was stirred at the same temperature for 24 h. The mixture was purified by silica gel flash column chromatography (CH$_2$Cl$_2$/MeOH=71:29 to 63:37) to give 5aa (48.1 mg, 45%, dr>10:1) as a colorless solid. Compound 5aa is a known compound.

Compound 5aa was also synthesized by procedure B. To a solution of pyrrolidine (12.0 µL, 0.146 mmol) in DMSO (350 µL), acetone (429 µL, 5.84 mmol) and boric acid (18.0 mg, 0.292 mmol) were added at room temperature (25° C.) and the mixture was stirred for 5 min. To this mixture, D-lactose monohydrate (100 mg, 0.278 mmol) was added and the mixture was stirred at the same temperature for 96 h. The mixture was purified by silica gel flash column chromatography (CH$_2$Cl$_2$/MeOH=71:29 to 63:37) to give 5aa (64.5 mg, 61%, dr>10:1) as a colorless solid.

Compound 5aa was also synthesized by procedure C but using 10 equiv of acetone (368 µL, 5.0 mmol) from D-lactose monohydrate (180 mg, 0.50 mmol), and purified by flash column chromatography (CH$_2$Cl$_2$/MeOH=70:30 to 65:35), colorless solid, 57 mg, 30%.

Rf=0.28 (CH$_2$Cl$_2$/MeOH=2:1). $^1$H NMR (400 MHz, CD$_3$OD): δ 4.36 (d, J=7.6 Hz, 1H), 3.85-3.75 (m, 3H), 3.75-3.63 (m, 2H), 3.62-3.46 (m, 6H), 3.39-3.34 (m, 1H), 3.15 (t, J=8.8 Hz, 1H), 2.90 (dd, J=16.4 Hz, 2.2 Hz, 1H), 2.61 (dd, J=16.4 Hz, 9.2 Hz, 1H), 2.20 (s, 3H). $^{13}$C NMR (100 MHz, CD$_3$OD): δ 210.0, 105.1, 80.8, 80.2, 77.9, 77.1, 74.81, 74.78, 72.6, 70.3, 62.5, 62.0, 47.0, 30.6. HRMS (ESI): calcd for C$_{15}$H$_{27}$O$_{11}$ ([M+H]$^+$) 383.1548, found 383.1530.

[Chem.42]

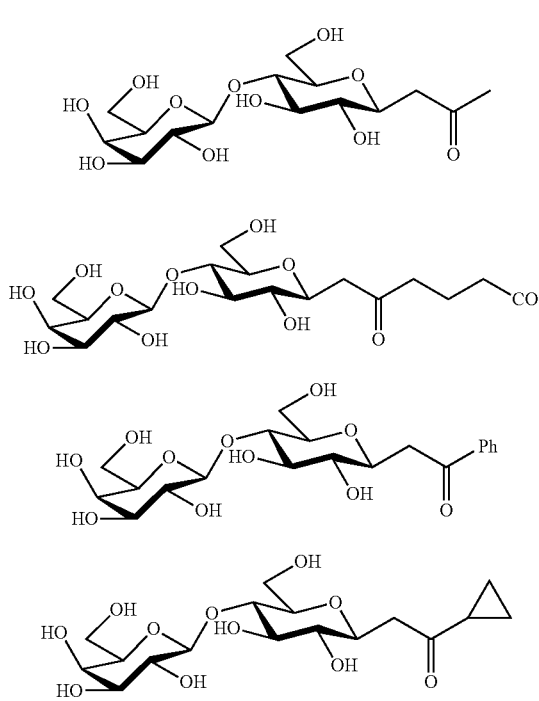

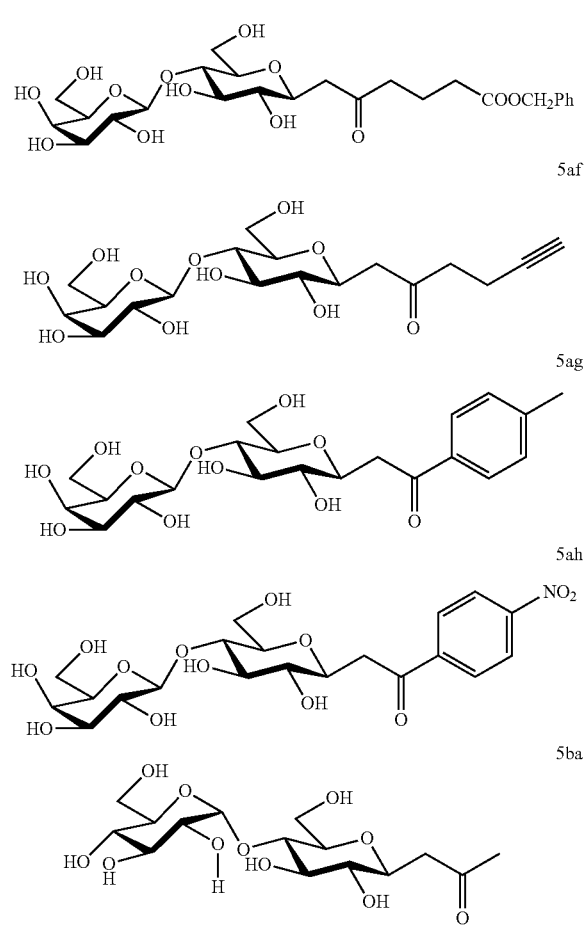

Compound 5ab was synthesized by procedure C from D-lactose and ethyl 5-oxohexanoate. A mixture of D-lactose monohydrate (180 mg, 0.50 mmol) and ethyl 5-oxohexanoate (320 µL, 2.0 mmol) in DMSO (1.0 mL) was stirred at room temperature (25° C.) for 5 min to solubilize the carbohydrate. To the solution, pyrrolidine (21 µL, 0.25 mmol) and H$_3$BO$_3$ (61 mg, 1.0 mmol) were added and the mixture was stirred at the same temperature for 48 h. The mixture was purified by silica gel flash column chromatography (CH$_2$Cl$_2$/MeOH=70:30 to 64:36) to give 5ab (109 mg, 45%, dr>20:1) as a colorless solid.

Compound 5ab was also synthesized by a modified procedure C from D-lactose and ethyl 5-oxohexanoate with reaction time for 96 h. A mixture of D-lactose monohydrate (180 mg, 0.50 mmol) and ethyl 5-oxohexanoate (320 µL, 2.0 mmol) in DMSO (1.0 mL) was stirred at room temperature (25° C.) for 5 min to solubilize the carbohydrate. To the solution, pyrrolidine (21 µL, 0.25 mmol) and H3BO3 (61 mg, 1.0 mmol) were added and the mixture was stirred at the same temperature for 96 h. The mixture was purified by silica gel flash column chromatography (CHCl$_3$/MeOH=65:35 to 60:40) to give 5ab (156 mg, 65%, dr>10:1) as a colorless solid.

Rf=0.27 (CH$_2$Cl$_2$/MeOH=2:1). $^1$H NMR (400 MHz, CD$_3$OD): δ 4.35 (d, J=7.5 Hz, 1H), 4.11 (q, J=7.1 Hz, 2H), 3.82-3.75 (m, 4H), 3.72-3.65 (m, 2H), 3.60-3.46 (m, 5H), 3.36-3.32 (m, 1H), 3.14 (dd, J=9.4 Hz, 8.8 Hz, 1H), 2.85 (dd, J=15.7 Hz, 2.9 Hz, 1H), 2.62-2.56 (m, 3H), 2.32 (t, J=7.2 Hz, 2H), 1.84 (quint, J=7.2 Hz, 2H), 1.24 (t, J=7.1 Hz, 3H). $^{13}$C NMR (100 MHz, CD$_3$OD): δ 211.0, 175.1, 105.0, 80.8, 80.1, 77.9, 77.2, 77.0, 74.8, 72.5, 70.2, 62.4, 61.9, 61.4, 46.3, 43.1, 34.0, 19.8, 14.5. HRMS (ESI): calcd for C$_{20}$H$_{35}$O$_{13}$ ([M+H]$^+$) 483.2072, found 483.2062.

Compound 5ac was synthesized by procedure C from D-lactose monohydrate (180 mg, 0.50 mmol) and acetophenone (233 μL, 2.0 mmol), and purified by flash column chromatography (CH$_2$Cl$_2$/MeOH=74:26 to 65:35), colorless solid, 80 mg, 36%, dr>10:1.

Rf=0.27 (CH$_2$Cl$_2$/MeOH=2:1). $^1$H NMR (400 MHz, (CD$_3$)$_2$SO): δ 7.96 (d, J=7.0 Hz, 2H), 7.63-7.61 (m, 1H), 7.54-7.50 (m, 2H), 5.25 (d, J=5.7 Hz, 1H), 5.09 (d, J=4.1 Hz, 1H), 4.77 (d, J=4.8 Hz, 1H), 4.70 (d, J=0.9 Hz, 1H), 4.64 (t, J=5.2 Hz, 1H), 4.51 (d, J=4.5 Hz, 1H), 4.37 (t, J=6.0 Hz, 1H), 4.21 (d, J=7.2 Hz, 1H), 3.73 (td, J=9.3 Hz, 2.4 Hz, 1H), 3.64-3.59 (m, 2H), 3.57-3.44 (m, 4H), 3.37-3.27 (m, 5H), 3.23-3.18 (m, 1H), 3.16-3.05 (m, 2H). $^{13}$C NMR (100 MHz, (CD$_3$)$_2$SO): δ 198.0, 136.9, 133.0, 128.6, 128.0, 103.8, 80.9, 78.6, 76.2, 75.57, 75.52, 73.25, 73.22, 70.5, 68.1, 60.5, 60.3, 41.0. HRMS (ESI): calcd for C$_{20}$H$_{29}$O$_{11}$ ([M+H]$^+$) 445.1704, found 445.1700.

Compound 5ad was synthesized by procedure C from D-lactose monohydrate (180 mg, 0.50 mmol) and cyclopropyl methyl ketone (198 μL, 2.0 mmol), and purified by flash column chromatography (CH$_2$Cl$_2$/MeOH=7:3 to 6:4), colorless solid, 92 mg, 45%.

Rf=0.27 (CH$_2$Cl$_2$/MeOH=2:1). $^1$H NMR (400 MHz, CD$_3$OD): δ 4.36 (d, J=7.5 Hz, 1H), 3.86-3.63 (m, 5H), 3.60-3.46 (m, 6H), 3.38-3.32 (m, 1H), 3.17 (dd, J=9.2 Hz, 8.8 Hz, 1H), 3.02 (dd, J=16.0 Hz, 2.6 Hz, 1H), 2.72 (dd, J=16.4 Hz, 9.2 Hz, 1H), 2.15-2.09 (m, 1H), 1.00-0.89 (m, 4H). $^{13}$C NMR (100 MHz, CD$_3$OD): δ 212.0, 105.0, 80.7, 80.1, 77.9, 77.0, 76.8, 74.7, 74.6, 72.5, 70.2, 62.4, 61.9, 46.6, 21.7, 11.5, 11.2. HRMS (ESI): calcd for C$_{17}$H$_{29}$O$_{11}$ ([M+H]$^+$) 409.1704, found 409.1698.

Compound 5ae was synthesized by procedure C from D-lactose monohydrate (180 mg, 0.50 mmol) and benzyl 5-oxohexanoate (440 mg, 2.0 mmol), and purified by flash column chromatography (CH$_2$Cl$_2$/MeOH=70:30 to 64:36), colorless gum, 95 mg, 35%.

Rf=0.27 (CH$_2$Cl$_2$/MeOH=2:1). $^1$H NMR (400 MHz, CD$_3$OD): δ 7.36-7.30 (m, 5H), 5.10 (s, 2H), 4.36 (d, J=7.6 Hz, 1H), 3.83 (dd, J=3.1 Hz, 0.7 Hz, 1H), 3.81-3.65 (m, 5H), 3.62-3.48 (m, 5H), 3.36-3.32 (m, 1H), 3.16 (dd, J=9.2 Hz, 8.8 Hz, 1H), 2.84 (dd, J=15.8 Hz, 2.9 Hz, 1H), 2.61-2.54 (m, 3H), 2.38 (t, J=7.2 Hz, 2H), 1.85 (quint, J=7.2 Hz, 2H). $^{13}$C NMR (100 MHz, CD$_3$OD): δ 211.0, 174.7, 137.5, 129.5, 129.1, 105.0, 80.8, 80.0, 77.7, 77.1, 76.9, 74.76, 74.70, 72.4, 70.2, 67.1, 62.4, 61.9, 46.2, 43.0, 34.0, 19.7. HRMS (ESI): calcd for C$_{25}$H$_{37}$O$_{13}$ ([M+H]$^+$) 545.2229, found 545.2210.

Compound 5af was synthesized by procedure C, from D-lactose monohydrate (180 mg, 0.50 mmol) and 5-hexyn-2-one (192 mg, 2.0 mmol), and purified by flash column chromatography (CH$_2$Cl$_2$/MeOH=75:25 to 70:30), colorless solid, 44 mg, 21%.

Rf=0.27 (CH$_2$Cl$_2$/MeOH=2:1). $^1$H NMR (400 MHz, CD$_3$OD): δ 4.35 (d, J=7.6 Hz, 1H), 3.84-3.80 (m, 3H), 3.80-3.75 (m, 1H), 3.72-3.64 (m, 2H), 3.60-3.46 (m, 6H), 3.36-3.32 (m, 1H), 3.15 (dd, J=9.6 Hz, 8.8 Hz, 1H), 2.87 (dd, J=16.0 Hz, 2.8 Hz, 1H), 2.82-2.74 (m, 2H), 2.62 (dd, J=16.0 Hz, 9.1 Hz, 1H), 2.39 (td, J=7.1 Hz, 2.6 Hz, 2H), 2.20 (t, J=2.6 Hz, 1H). $^{13}$C NMR (100 MHz, CD$_3$OD): δ 209.2, 105.0, 84.0, 80.7, 80.1, 77.9, 77.1, 77.0, 74.8, 72.5, 70.3, 69.6, 62.5, 61.9, 46.2, 43.1, 13.3. HRMS (ESI): calcd for C$_{18}$H$_{29}$O$_{11}$ ([M+H]$^+$) 421.1704, found 421.1698.

Compound 5ag was synthesized by procedure C from D-lactose monohydrate (180 mg, 0.50 mmol) and 4'-methylacetophenone (267 μL, 2.0 mmol), and purified by flash column chromatography (CH$_2$Cl$_2$/MeOH=74:26 to 65:35), colorless solid, 80 mg, 35%.

Compound 5ag was also synthesized by procedure C except that the reaction was carried out for 96 h from D-lactose monohydrate (180 mg, 0.50 mmol) and 4'-methylacetophenone (267 μL, 2.0 mmol), and purified by flash column chromatography (CH$_2$Cl$_2$/MeOH=74:26 to 65:35), colorless solid, 126 mg, 55%.

Rf=0.27 (CH$_2$Cl$_2$/MeOH=2:1). $^1$NMR (400 MHz, CD$_3$OD): δ 7.90 (d, J=8.0 Hz, 2H), 7.31 (d, J=8.0 Hz, 2H), 4.36 (d, J=7.5 Hz, 1H), 3.86-3.73 (m, 6H), 3.71 (dd, J=11.6 Hz, 4.8 Hz, 1H), 3.62-3.51 (m, 5H), 3.49 (dd, J=10.0 Hz, 3,6 Hz, 1H), 3.37-3.33 (m, 1H), 3.28-3.20 (m, 1H), 2.40 (s, 3H). $^{13}$C NMR (100 MHz, CD$_3$OD): δ 200.2, 145.5, 136.0, 130.2, 129.5, 105.0, 80.7, 80.1, 78.0, 77.2, 77.0, 74.79, 74.76, 72.5, 70.3, 62.5, 61.8, 42.1, 21.6. HRMS (ESI): calcd for C$_{21}$H$_{31}$O$_{11}$ ([M+H]$^+$) 459.1861, found 459.1852.

Compound 5ah was synthesized by procedure C from D-lactose monohydrate (180 mg, 0.50 mmol) and 4'-nitroacetophenone (330 mg, 2.0 mmol), and purified by column chromatography (CH$_2$Cl$_2$/MeOH=68:32 to 60:40), colorless solid, 61 mg, 25%.

Rf=0.27 (CH$_2$Cl$_2$/MeOH=2:1). $^1$NMR (400 MHz, (CD$_3$)$_2$SO): δ 8.32 (d, J=8.9 Hz, 2H), 8.17 (d, J=8.9 Hz, 2H), 5.32 (d, J=5.6 Hz, 1H), 5.11 (d, J=3.7 Hz, 1H), 4.81 (s, 1H), 4.73 (s, 1H), 4.68-4.67 (m, 1H), 4.55 (d, J=4.5 Hz, 1H), 4.42 (t, J=5.9 Hz, 1H), 4.21 (d, J=7.3 Hz, 1H), 3.70 (td, J=9.1 Hz, 2.7 Hz, 1H), 3.65-3.58 (m, 2H), 3.57-3.44 (m, 4H), 3.41-3.28 (m, 5H), 3.23-3.15 (m, 2H), 3.13-3.06 (m, 1H). $^{13}$C NMR (100 MHz, (CD$_3$)$_2$SO): δ 197.6, 149.8, 141.7, 129.5, 123.8, 103.8, 80.8, 78.7, 76.1, 75.6, 75.5, 73.3, 73.2, 70.6, 68.1, 60.5, 60.3, 41.8. HRMS (ESI): calcd for C$_{20}$H$_{28}$NO$_{13}$ ([M+H]$^+$) 490.1555, found 490.1557.

Compound 5ba was synthesized by a modified procedure A from D-maltose monohydrate and acetone. To a solution of pyrrolidine (11.0 μL. 0.134 mmol) in DMSO (1.0 mL), acetone (408 μL, 5.55 mmol) and boric acid (17.0 mg, 0.277 mmol) were added at room temperature (25° C.) and the mixture was stirred for 5 min. To this mixture, D-maltose monohydrate (100 mg, 0.277 mmol) was added and the mixture was stirred at the same temperature for 96 h. The mixture was purified by silica gel flash column chromatography (CH$_2$Cl$_2$/MeOH=70:30 to 63:37) to give 5ba (49.1 mg, 46%, dr>10:1) as a pale yellow gum. Compound 5ba is a known compound.

Rf=0.38 (CH$_2$Cl$_2$/MeOH=2:1). $^1$NMR (400 MHz, CD$_3$OD): δ 5.16 (d, J=3.6 Hz, 1H), 3.86-3.74 (m, 3H), 3.72-3.58 (m, 5H), 3.52 (t, J=9.2 Hz, 1H), 3.45 (dd, J=9.8 Hz, 3.8 Hz, 1H), 3.35-3.24 (m, 2H), 3.13 (t, J=9.2 Hz, 1H), 2.88 (dd, J=16.0 Hz, 2.8 Hz, 1H), 2.61 (dd, J=16.0 Hz, 9.0 Hz, 1H), 2.21 (s, 3H). $^{13}$C NMR (100 MHz, CD$_3$OD): δ 210.2, 102.8, 81.4, 80.3, 79.4, 77.2, 75.0, 74.69, 74.66, 74.2, 71.5, 62.7, 62.2, 47.0, 30.6. HRMS (ESI): calcd for C$_{15}$H$_{27}$O$_{11}$ ([M+H]$^+$) 383.1548, found 383.1538.

Compound 5ca was synthesized by procedure A from D-cellobiose and acetone. To a solution of pyrrolidine (12.0 μL, 0.146 mmol) in DMSO (1.0 mL), acetone (429 μL, 5.84 mmol) and boric acid (18.0 mg, 0.292 mmol) were added at room temperature (25° C.) and the mixture was stirred for 5 min. To this mixture, D-cellobiose (100 mg, 0.292 mmol) was added and the mixture was stirred at the same temperature for 48 h. The mixture was purified by silica gel flash column chromatography (CH$_2$Cl$_2$/MeOH=76:24 to 66:34) to give 5ca (58.7 mg, 53%, dr>10:1) as a pale yellow solid. Compound 5ca is a known compound.

Rf=0.43 (CH$_2$Cl$_2$/MeOH=2:1). NMR (400 MHz, CD$_3$OD): δ 4.10 (d, 1H, J=8.0 Hz), 3.88 (dd, J=11.6 Hz, 2.0 Hz, 1H), 3.85-3.78 (m, 2H), 3.72-3.63 (m, 2H), 3.54 (t, J=9.0 Hz, 2H), 3.49 (t, J=8.6 Hz, 1H), 3.41-3.28 (m, 4H), 3.24 (dd, J=8.8 Hz, 8.0 Hz, 1H), 3.15 (dd, J=9.2 Hz, 8.8 Hz, 1H), 2.89 (dd, J=16.4 Hz, 2.8 Hz, 1H), 2.61 (dd, J=16.4 Hz, 9.2 Hz, 1H), 2.20 (s, 3H). $^{13}$C NMR (100 MHz, CD$_3$OD): δ 210.4, 104.5, 80.8, 80.1, 78.0, 77.8, 77.7, 76.9, 74.9, 74.8, 71.3, 62.4, 61.9, 47.0, 30.7. HRMS (ESI): calcd for C$_{15}$H$_{27}$O$_{11}$ ([M+H]$^+$) 383.1548, found 383.1548.

Compound 7aa was synthesized by a modified procedure C from 3'-sialyllactose sodium salt and acetone. To a solution of pyrrolidine (13.0 μL, 0.158 mmol) in DMSO (370 μL), acetone (448 μL, 6.09 mmol) and boric acid (38.0 mg, 0.614 mmol) were added at room temperature (25° C.) and the mixture was stirred for 5 min. To this mixture, 3'-sialyllactose sodium salt (200 mg, 0.305 mmol) was added and the mixture was stirred at the same temperature for 96 h. The mixture was purified by silica gel flash column chromatography (CH$_2$Cl$_2$/MeOH=61:39 to 45:55) to give 7aa (151.4 mg, 74%, dr>10:1) as a pale yellow gum.

Rf=0.53 (CH$_2$Cl$_2$/MeOH=1:1). $^1$H NMR (400 MHz, CD$_3$OD): δ 4.43 (d, J=7.6 Hz, 1H), 4.05 (dd, J=9.6 Hz, 3.2 Hz, 1H), 3.95-3.91 (m, 1H), 3.89-3.47 (m, 16H), 3.39-3.34 (m, 1H), 3.14 (t, J=9.0 Hz, 1H), 2.89 (dd, J=16.0 Hz, 2.8 Hz, 1H), 2.86 (d, J=12.4 Hz, 4.0 Hz, 1H), 2.61 (dd, J=16.0 Hz, 9.2 Hz, 1H), 2.20 (s, 3H), 2.01 (s, 3H), 1.79-1.68 (m, 1H). $^{13}$C NMR (100 MHz, CD$_3$OD) δ 210.2, 175.5, 174.9, 105.1, 101.1, 81.3, 80.2, 77.8, 77.6, 77.2, 77.0, 74.9, 74.8, 73.0, 70.8, 70.1, 69.4, 69.0, 64.6, 62.7, 62.2, 54.0, 47.1, 42.1, 30.6, 22.6. HRMS (ESI): calcd for C$_{26}$H$_{44}$NO$_{19}$ ([M+H]$^+$) 674.2502, found 674.2493.

[Chem.43]

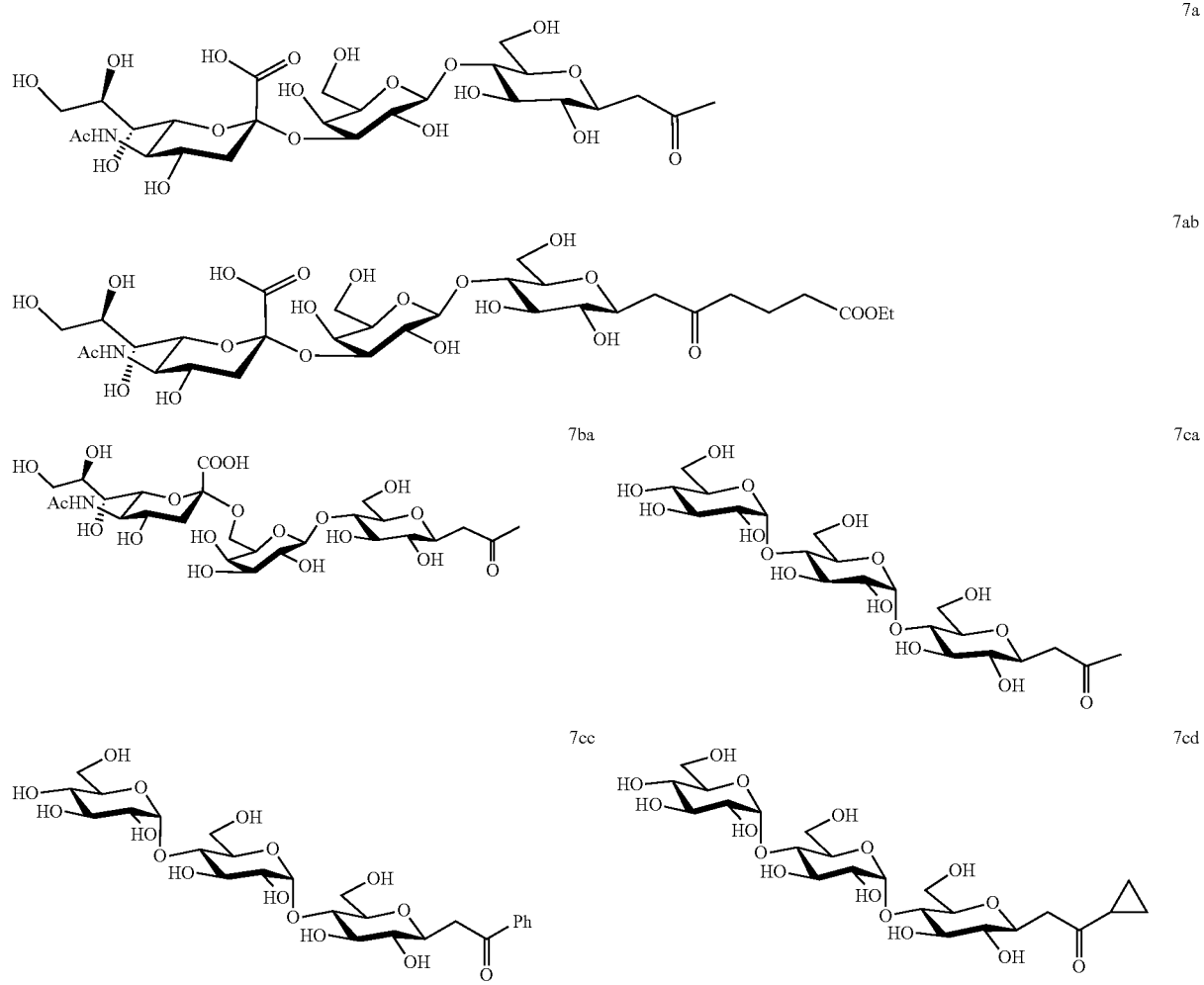

7cg

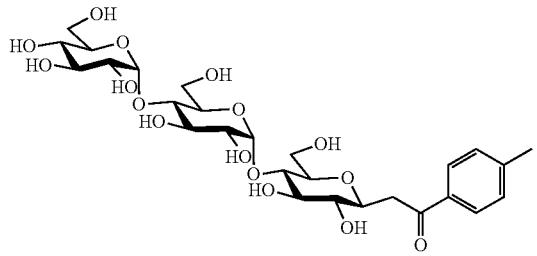

7ci

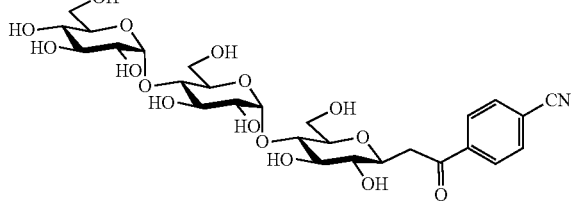

Compound 7ab was synthesized by procedure C except that the reaction was carried out in a 0.25 mmol-scale and for 42 h from 3'-sialyllactose sodium salt (164 mg, 0.25 mmol) and ethyl 5-oxohexanoate (160 µL, 1.0 mmol), and purified by column chromatography (CHCl$_3$/MeOH=45:55 to 30:70), colorless gum, 80 mg, 40%.

Rf=0.27 (CH$_2$Cl$_2$/MeOH=1:1). $^1$H NMR (400 MHz, CD$_3$OD): δ 4.42 (d, J=7.9 Hz, 1H), 4.11 (q, J=7.1 Hz, 2H), 4.04 (dd, J=9.7 Hz, 3.1 Hz, 1H), 3.92 (brd, J=2.8 Hz, 1H), 3.87-3.55 (m, 14H), 3.53-3.47 (m, 2H), 3.37-3.33 (m, 1H), 3.14 (t, J=9.1 Hz, 1H), 2.87-2.80 (m, 2H), 2.67-2.53 (m, 3H), 2.32 (t, J=7.1 Hz, 2H), 2.01 (s, 3H), 1.84 (quint, J=7.1 Hz, 2H), 1.77-1.69 (m, 1H), 1.24 (t, J=7.1 Hz, 3H). $^{13}$C NMR (100 MHz, CD$_3$OD): δ 211.1, 175.4, 175.1, 174.9, 105.0, 101.0, 81.0, 80.1, 77.7, 77.5, 77.2, 76.9, 74.9, 74.8, 72.9, 70.7, 70.0, 69.2, 68.9, 64.4, 62.6, 62.0, 61.4, 53.9, 46.3, 43.1, 42.0, 34.0, 22.6, 19.7, 14.5. HRMS (ESI): calcd for C$_{31}$H$_{52}$O$_{21}$N ([M+H]$^+$) 774.3026, found 774.3020.

Compound 7ba was synthesized by a modified procedure C from 6'-sialyllactose sodium salt and acetone. To a solution of pyrrolidine (13.0 µL, 0.158 mmol) in DMSO (370 µL), acetone (448 µL, 6.09 mmol) and boric acid (38.0 mg, 0.614 mmol) were added at room temperature (25° C.) and the mixture was stirred for 5 min. To this mixture, 6'-sialyllactose sodium salt (200 mg, 0.305 mmol) was added and the mixture was stirred at the same temperature for 96 h. The mixture was purified by silica gel flash column chromatography (CH$_2$Cl$_2$/MeOH=54:46 to 33:67) to give 7ba (164.4 mg, 80%, dr>10:1) as a pale yellow gum.

Rf=0.23 (CH$_2$Cl$_2$/MeOH=1:1). $^1$H NMR (400 MHz, CD$_3$OD): δ 4.33 (d, J=7.2 Hz, 1H), 4.06 (dd, J=9.8 Hz, 7.8 Hz, 1H), 3.94-3.46 (m, 17H), 3.42-3.36 (m, 1H), 3.24-3.17 (m, 1H), 2.93 (dd, J=16.0, 2.8 Hz, 1H), 2.80 (dd, J=12.0 Hz, 4.4 Hz, 1H), 2.63 (dd, J=16.0 Hz, 8.8 Hz, 1H), 2.21 (s, 3H), 2.01 (s, 3H), 1.66 (t, J=12.0 Hz, 1H). $^{13}$C NMR (100 MHz, CD$_3$OD) δ 210.3, 175.0, 174.6, 105.2, 101.5, 81.8, 80.1, 77.8, 76.8, 75.7, 75.0, 74.7, 74.2, 73.2, 72.4, 70.6, 70.3, 69.7, 64.63, 64.55, 62.2, 53.9, 47.0, 42.3, 30.7, 22.9. HRMS (ESI): calcd for C$_{26}$H$_{44}$NO$_{19}$ ([M+H]$^+$) 674.2502, found 674.2491.

Compound 7ca was synthesized by a modified procedure A from D-maltotriose and acetone. To a solution of pyrrolidine (8.0 µL, 0.097 mmol) in DMSO (1.0 mL), acetone (292 µL, 3.97 mmol) and boric acid (12.0 mg, 0.194 mmol) were added at room temperature (25° C.) and the mixture was stirred for 5 min. To this mixture, D-maltotriose (100 mg, 0.198 mmol) was added and the mixture was stirred at the same temperature for 96 h. The mixture was purified by silica gel flash column chromatography (CH$_2$Cl$_2$/MeOH=70:30 to 63:37) to give 7ca (37.9 mg, 35%, dr>10:1) as a pale yellow gum.

Rf=0.20 (CH$_2$Cl$_2$/MeOH=2:1). $^1$H NMR (400 MHz, CD$_3$OD): δ 5.165 (d, J=3.6 Hz, 1H), 5.159 (d, J=3.6 Hz, 1H), 3.90-3.59 (m, 12H), 3.54-3.43 (m, 4H), 3.35-3.24 (m, 2H), 3.13 (t, J=9.4 Hz, 1H), 2.88 (dd, J=16.2 Hz, 2.8 Hz, 1H), 2.61 (dd, J=16.2 Hz, 9.2 Hz, 1H), 2.21 (s, 3H). $^{13}$C NMR (100 MHz, CD$_3$OD): δ 210.2, 102.8, 102.6, 81.4, 81.2, 80.2, 79.3, 77.2, 75.0, 74.9, 74.71, 74.65, 74.2, 73.8, 73.3, 71.4, 62.7, 62.3, 62.1, 47.0, 30.7. HRMS (ESI): calcd for C$_{21}$H$_{37}$O$_{16}$ ([M+H]$^+$) 545.2076, found 545.2067.

Compound 7cc was synthesized by procedure C except that the reaction was carried out in a 0.25 mmol-scale from D-maltotriose (126 mg, 0.25 mmol) and acetophenone (117 µL, 1.0 mmol), and purified by flash column chromatography (CH$_2$Cl$_2$/MeOH=60:40 to 50:50), colorless gum, 33 mg, 22%.

Rf=0.27 (CH$_2$Cl$_2$/MeOH=1:1). $^1$H NMR (400 MHz, CD$_3$OD): δ 8.01 (d, J=7.2 Hz, 2H), 7.60 (tt, J=7.4 Hz, 1.2 Hz, 1H), 7.49 (t, J=7.4 Hz, 2H), 5.18 (d, J=4.0 Hz, 1H), 5.16 (d, J=3.7 Hz, 1H), 3.91-3.80 (m, 5H), 3.79-3.73 (m, 3H), 3.72-3.43 (m, 9H), 3.41-3.19 (m, 4H). $^{13}$C NMR (100 MHz, CD$_3$OD): δ 200.5, 138.5, 134.3, 129.7, 129.3, 102.8, 102.6, 81.4, 81.2, 80.1, 79.4, 77.2, 75.0, 74.9, 74.7, 74.6, 74.2, 73.8, 73.2, 71.4, 62.7, 62.1, 42.2. HRMS (ESI): calcd for C$_{26}$H$_{39}$O$_{16}$ ([M+H]$^+$) 607.2233, found 607.2216.

Compound 7cd was synthesized by procedure C except that the reaction was carried out in a 0.25 mmol-scale from D-maltotriose (126 mg, 0.25 mmol) and cyclopropyl methyl ketone (100 µL, mmol), and purified by flash column chromatography (CH$_2$Cl$_2$/MeOH=65:35 to 50:50), colorless gum, 42 mg, 30%.

Rf=0.27 (CH$_2$Cl$_2$/MeOH=1:1). $^1$H NMR (400 MHz, CD$_3$OD): δ 5.19-5.15 (m, 2H), 3.89-3.81 (m, 4H), 3.81-3.60 (m, 8H), 3.58-3.44 (m, 4H), 3.35-3.25 (m, 2H), 3.16 (td, J=9.0 Hz, 2.4 Hz, 1H), 3.02 (d, J=16.2 Hz, 1H), 2.76-2.69 (m, 1H), 2.15-2.09 (m, 1H), 0.98-0.93 (m, 4H). $^{13}$C NMR (100 MHz, CD$_3$OD): δ 212.1, 102.7, 102.6, 81.3, 81.2, 80.1, 79.3, 76.9, 75.0, 74.9, 74.7, 74.5, 74.1, 73.7, 73.2, 71.4, 62.6, 62.1, 62.0, 46.6, 21.7, 11.6, 11.3. HRMS (ESI): calcd for C$_{23}$H$_{39}$O$_{16}$ ([M+H]$^+$) 571.2233, found 571.2231.

Compound 7cg was synthesized by procedure C except that the reaction was carried out in a 0.25 mmol-scale from D-maltotriose (126 mg, 0.25 mmol) and 4'-methylacetophenone (134 µL, 1.0 mmol), and purified by flash column chromatography (CH$_2$Cl$_2$/MeOH=60:40 to 50:50), colorless gum, 39 mg, 25%.

Rf=0.27 (CH$_2$Cl$_2$/MeOH=1:1). $^1$H NMR (400 MHz, CD$_3$OD): δ 7.90 (d, J=8.0 Hz, 2H), 7.31 (d, J=8.0 Hz, 2H), 5.17 (d, J=3.8 Hz, 1H), 5.15 (d, J=3.8 Hz, 1H), 3.91-3.80 (m, 5H), 3.78-3.72 (m, 3H), 3.70-3.67 (m, 2H), 3.66-3.63 (m, 1H), 3.63-3.56 (m, 2H), 3.54-3.52 (m, 1H), 3.51-3.48 (m, 1H), 3.45 (dd, J=9.7 Hz, 3.7 Hz, 1H), 3.39 (dd, J=16.4 Hz, 2.3 Hz, 1H), 3.34-3.31 (m, 1H), 3.30-3.23 (m, 2H), 3.19 (dd,

J=16.4 Hz, 8.9 Hz, 1H), 2.40 (s, 3H). $^{13}$C NMR (100 MHz, CD$_3$OD): δ 200.2, 145.5, 135.9, 130.3, 129.5, 102.8, 102.6, 81.4, 81.3, 80.1, 79.4, 77.2, 75.0, 74.9, 74.7, 74.6, 74.2, 73.8, 73.2, 71.5, 62.6, 62.13, 62.10, 42.1, 21.6. HRMS (ESI): calcd for C$_{27}$H$_{41}$O$_{16}$ ([M+H]$^+$) 621.2389, found 621.2374.

Compound 7ci was synthesized by procedure C except that the reaction was carried out in a 0.25 mmol-scale from D-maltotriose (126 mg, 0.25 mmol) and 4'-cyanoacetophenone (145 mg, 1.0 mmol), and purified by flash column chromatography (CH$_2$Cl$_2$/MeOH=60:40 to 49:51), colorless gum, 35 mg, 22%.

Rf=0.27 (CH$_2$Cl$_2$/MeOH=1:1). $^1$H NMR (400 MHz, CD$_3$OD): δ 8.08 (d, J=8.2 Hz, 2H), 7.81 (d, J=8.2 Hz, 2H), 5.14-5.11 (m, 2H), 3.85-3.76 (m, 5H), 3.73-3.66 (m, 3H), 3.64-3.54 (m, 5H), 3.52-3.35 (m, 5H), 3.26-3.21 (m, 3H). $^{13}$C NMR (100 MHz, CD$_3$OD): δ 199.2, 141.6, 133.6, 129.9, 118.9, 117.1, 102.7, 102.5, 81.2, 81.1, 80.1, 79.3, 77.0, 74.9, 74.8, 74.6, 74.5, 74.0, 73.7, 73.1, 71.3, 62.5, 62.08, 62.04, 42.2. HRMS (ESI): calcd for C$_{27}$H$_{38}$NO$_{16}$ ([M+H]$^+$) 632.2185, found 632.2174.

3. Transformations of the C-Glycoside Ketones (Schemes 3, 4, and 5)

Compound 8a

To a mixture of L-proline (8.0 mg, 0.069 mmol) in DMSO (0.5 mL), 6-methoxy-2-napthaldehyde (24.4 mg, 0.131 mmol) and N,N-diisopropylethylamine (11.0 μL, 0.063 mmol) were added at room temperature (25° C.), and the mixture was stirred for 5 min. To this mixture, compound 5aa (50.0 mg, 0.131 mmol) was added and the mixture was stirred at the same temperature for 96 h. The mixture was purified by silica gel flash column chromatography (CH$_2$Cl$_2$/MeOH=86:14 to 79:21) to give 8a (38.0 mg, 53%) as a pale yellow solid.

To a solution of pyrrolidine (5.0 μL, 0.061 mmol) in DMSO (1.0 mL), 6-methoxy-2-naphthaldehyde (24.4 mg, 0.131 mmol) and boric acid (4.0 mg, 0.065 mmol) were added at room temperature (25° C.) and the mixture was stirred for 5 min. To this mixture, compound 5aa (50.0 mg, 0.131 mmol) was added and the mixture was stirred at the same temperature for 96 h. The mixture was purified by silica gel flash column chromatography ((CH$_2$Cl$_2$/MeOH=86:14 to 79:21) to give 8a (27.3 mg, 38%) as a pale yellow solid.

Rf=0.32 (CH$_2$Cl$_2$/MeOH=4:1). $^1$H NMR (400 M Hz, CD$_3$OD): δ 7.98 (s, 1H), 7.82-7.71 (m, 4H), 7.24 (d, J=2.4 Hz, 1H), 7.15 (dd, J=9.0 Hz, 2.6 Hz, 1H), 6.96 (d, J=16.4 Hz, 1H), 4.39 (d, J=7.2 Hz, 1H), 3.91 (s, 3H), 3.91-3.45 (m, 11H), 3.43-3.37 (m, 1H), 3.31-3.25 (m, 1H), 3.17 (dd, J=16.0 Hz, 2.4 Hz, 1H), 2.96 (dd, J=16.0 Hz, 8.8 Hz, 1H). $^{13}$C NMR (100 MHz, CD$_3$OD) δ 201.1, 160.5, 145.5, 137.5, 131.7, 131.23, 131.16, 130.1, 128.7, 126.5, 125.2, 120.5, 107.1, 105.1, 80.8, 80.1, 77.9, 77.3, 77.0, 74.8, 74.7, 72.5, 70.3, 62.5, 61.9, 55.9, 44.1. HRMS (ESI): calcd for C$_{27}$H$_{35}$O$_{12}$ ([M+H]$^+$) 551.21230, found 551.21002.

[Chem.44]

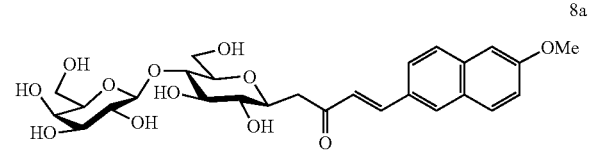

8a

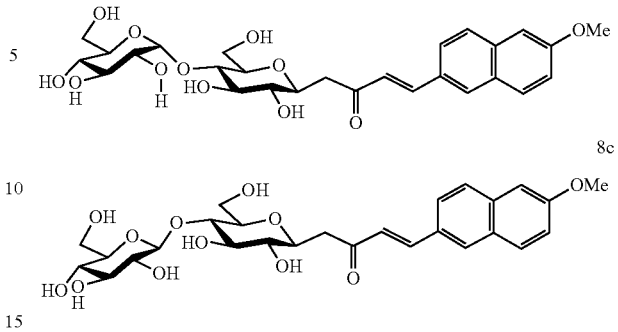

Compound 8b

To a solution of pyrrolidine (5.0 μL, 0.061 mmol) in DMSO (1.0 mL), 6-methoxy-2-napthaldehyde (24.4 mg, 0.131 mmol) and boric acid (4.0 mg, 0.065 mmol) were added at room temperature (25° C.) and the mixture was stirred for 5 min. To this mixture, compound 5ba (50.0 mg, 0.131 mmol) was added and the mixture was stirred at the same temperature for 96 h. The mixture was purified by silica gel flash column chromatography (CH$_2$Cl$_2$/MeOH=90:10 to 82:18) to give 8b (30.1 mg, 42%) as a pale yellow gum.

Rf=0.47 (CH$_2$Cl$_2$/MeOH=4:1). $^1$H NMR (400 MHz, CD$_3$OD): δ 8.00 (s, 1H), 7.82-7.77 (m, 2H), 7.80 (d, J=16.4 Hz, 1H), 7.74 (dd, J=8.8 Hz, 1.6 Hz, 1H), 7.25 (d, J=2.0 Hz, 1H), 7.16 (dd, J=8.8 Hz, 2.6 Hz, 1H), 6.97 (d, J=16.4 Hz, 1H), 5.18 (d, J=4.0 Hz, 1H), 3.92 (s, 3H), 3.86-3.75 (m, 4H), 3.75-3.53 (m, 5H), 3.46 (dd, J=9.2 Hz, 4.0 Hz, 1H), 3.37-3.31 (m, 1H), 3.30-3.22 (m, 2H), 3.16 (dd, J=15.6 Hz, 2.6 Hz, 1H), 2.95 (dd, J=15.6 Hz, 9.2 Hz, 1H). $^{13}$C NMR (100 MHz, CD$_3$OD) δ 201.1, 160.6, 145.5, 137.6, 131.6, 131.3, 130.2, 128.7, 126.5, 125.3, 120.5, 107.2, 102.9, 81.5, 80.3, 79.5, 77.6, 75.1, 74.81, 74.75, 74.3, 71.1, 62.8, 62.2, 55.9, 44.3. HRMS (ESI): calcd for C$_{27}$H$_{35}$O$_{12}$ ([M+H]$^+$) 551.21230, found 551.21008.

Compound 8c

To a mixture of L-proline (8.0 mg, 0.069 mmol) in DMSO (1.0 mL), 6-methoxy-2-napthaldehyde (24.0 mg, 0.129 mmol) and N,N-diisopropylethylamine (11.0 μL, mmol) were added at room temperature (25° C.), and the mixture was stirred for 5 min. To this mixture, compound 5ca (50.0 mg, 0.131 mmol) was added and the mixture was stirred at the same temperature for 96 h. The mixture was purified by silica gel flash column chromatography (CH$_2$Cl$_2$/MeOH=86:14 to 79:21) to give 8c (19.0 mg, 27%) as a pale yellow solid.

Rf=0.66 (CH$_2$Cl$_2$/MeOH=4:1). $^1$H NMR (400 MHz, CD$_3$OD): δ 7.99 (s, 1H), 7.81-7.77 (m, 2H), 7.80 (d, J=16.2 Hz, 1H), 7.74 (dd, J=8.8 Hz, 1.6 Hz, 1H), 7.25 (d, J=2.4 Hz, 1H), 7.16 (dd, J=8.8 Hz, 2.4 Hz, 1H), 6.97 (d, J=16.2 Hz, 1H), 4.43 (d, J=8.0 Hz, 1H), 3.92 (s, 3H), 3.92-3.77 (m, 4H), 3.68 (dd, J=12.0 Hz, 5.6 Hz, 1H), 3.60 (t, J=8.8 Hz, 1H), 3.54 (t, J=8.8 Hz, 1H), 3.41-3.31 (m, 4H), 3.30-3.21 (m, 2H), 3.15 (dd, J=15.8 Hz, 2.6 Hz, 1H), 2.96 (dd, J=15.8 Hz, 9.0 Hz, 1H). $^{13}$C NMR (100 MHz, CD$_3$OD) δ 201.1, 160.6, 145.5, 137.6, 131.7, 131.3, 131.2, 130.2, 128.7, 126.5, 125.3, 120.5, 107.1, 104.6, 80.8, 80.2, 78.1, 78.0, 77.8, 77.4, 74.9, 71.4, 62.4, 61.9, 55.9, 44.2. HRMS (ESI): calcd for $C_{27}H_{35}O_{12}$ ([M+H]$^+$) 551.21230, found 551.21227.

Compound 8d

To a solution of pyrrolidine (3.0 μL, 0.037 mmol) in DMSO (1.0 mL), 6-methoxy-2-napthaldehyde (14.0 mg, 0.075 mmol) and boric acid (5.0 mg, 0.081 mmol) were added at room temperature (25° C.) and the mixture was stirred for 5 min. To this mixture, compound 7aa (50.0 mg, 0.074 mmol) was added and the mixture was stirred at the same temperature for 48 h. The mixture was purified by silica gel flash column chromatography ($CH_2Cl_2$/MeOH=69:31 to 51:49) to give 8d (24.6 mg, 40%) as a pale yellow solid.

Rf=0.16 ($CH_2Cl_2$/MeOH=2:1). $^1$H NMR (400 MHz, $CD_3OD$): δ 7.99 (s, 1H), 7.82-7.76 (m, 2H), 7.80 (d, J=16.0 Hz, 1H), 7.74 (dd, J=8.8 Hz, 1.6 Hz, 1H), 7.25 (d, 1H, J=2.4 Hz), 7.16 (dd, J=8.8 Hz, 2.4 Hz, 1H), 6.96 (d, J=16.0 Hz, 1H), 4.45 (d, J=8.0 Hz, 1H), 4.06 (dd, J=9.6 Hz, 3.2 Hz, 1H), 3.94-3.46 (m, 17H), 3.92 (s, 3H), 3.42-3.37 (m, 1H), 3.26 (dd, J=9.6 Hz, 8.8 Hz, 1H), 3.15 (dd, J=15.6 Hz, 2.4 Hz, 1H), 2.95 (dd, J=15.6 Hz, 9.0 Hz, 1H), 2.89-2.83 (m, 1H), 2.01 (s, 3H), 1.79-1.68 (m, 1H). $^{13}$C NMR (100 MHz, $CD_3OD$) δ 201.1, 175.5, 174.9, 160.6, 145.4, 137.5, 131.6, 131.2, 130.2, 128.7, 126.5, 125.3, 120.5, 107.1, 105.0, 101.1, 81.1, 80.2, 77.9, 77.6, 77.5, 77.0, 74.9, 74.8, 73.0, 70.8, 70.1, 69.3, 69.0, 64.5, 62.7, 62.0, 55.9, 53.9, 44.2, 42.1, 22.6. HRMS (ESI): calcd for $C_{38}H_{52}NO_{20}$([M+H]$^+$) 842.3077, found 842.3051.

1H), 6.97 (d, J=16.0 Hz, 1H), 4.33 (d, J=7.6 Hz, 1H), 4.07 (dd, J=10.0 Hz, 8.0 Hz, 1H), 3.92 (s, 3H), 3.92-3.45 (m, 17H), 3.43-3.37 (m, 1H), 3.36-3.30 (m, 1H), 3.19 (dd, J=16.0 Hz, 2.4 Hz, 1H), 2.96 (dd, J=16.0 Hz, 8.8 Hz, 1H), 2.82 (dd, J=12.0 Hz, 4.8 Hz, 1H), 2.00 (s, 3H), 1.68 (1, J=12.0 Hz, 1H). $^{13}$C NMR (100 MHz, $CD_3OD$) δ 201.2, 174.9, 174.5, 160.6, 145.5, 137.6, 131.7, 131.3, 131.2, 130.2, 128.7, 126.5, 125.3, 120.5, 107.1, 105.2, 101.5, 81.7, 80.0, 77.9, 77.2, 75.8, 75.0, 74.6, 74.2, 73.2, 72.5, 70.6, 70.3, 69.8, 64.64, 64.61, 62.1, 55.9, 53.8, 44.2, 42.5, 22.8. HRMS (ESI): calcd for $C_{38}H_{52}NO_{20}$ ([M+H]$^+$) 842.3077, found 842.3055.

Compound 9

A mixture of 4a (50 mg, 0.13 mmol) and p-toluenesulfonyl hydrazide (32 mg, 0.17 mmol) in EtOH (1.0 mL) was stirred at room temperature (25° C.) for 18 h. The mixture was purified silica gel flash column chromatography ($CH_2Cl_2$/MeOH=87:13 to 80:20) to give 9 (41 mg, 57%) as a light brown solid.

Rf=0.26 ($CH_2Cl_2$/MeOH (5:1). $^1$H NMR (400 MHz, $CD_3OD$) δ 7.82 (d, J=8.0 Hz, 2H×⅖), 7.80 (d, J=8.0 Hz, 2H×⅗), 7.39-7.34 (m, 2H), 4.35 (d, J=7.6 Hz, 1H), 3.85-3.37 (m, 11H), 3.34-3.26 (m, 1H×⅖), 3.21-3.16 (m, 1H×⅗), 3.09 (t, J=8.8 Hz, 1H×⅗), 3.07 (t, J=8.8 Hz, 1H×⅖), 2.73 (dd, J=14.8 Hz, 2.8 Hz, 1H×⅗), 2.65-2.55 (m, 2H×2/5), 2.42 (s, 3H), 2.27 (dd, J=14.8 Hz, 9.2 Hz, 1H×⅗), 1.94 (s, 3H×⅖), 1.86 (s, 3H×⅗). $^{13}$C NMR (100 MHz, $CD_3OD$) δ 159.3, 159.1, 145.2, 145.1, 137.6, 137.3, 130.5, 130.4,

[Chem.45]

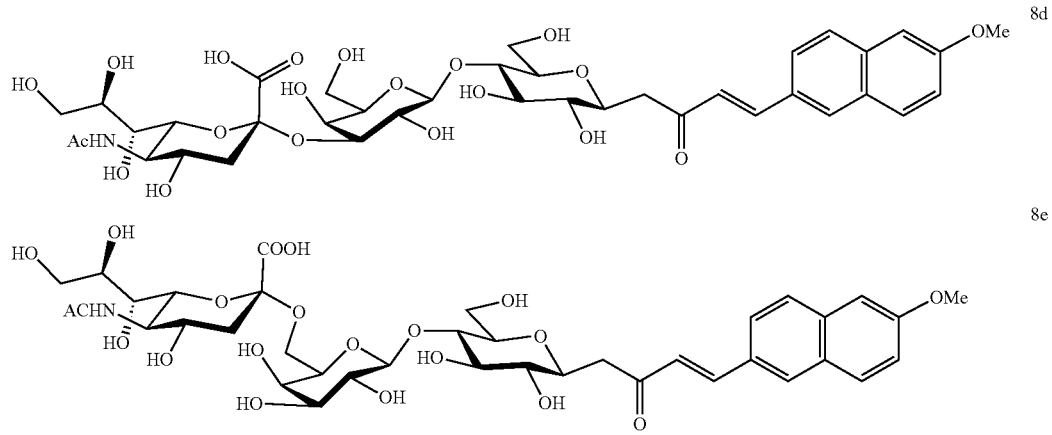

Compound 8e

To a solution of pyrrolidine (3.0 μL, 0.037 mmol) in DMSO (1.0 mL), 6-methoxy-2-napthaldehyde (14.0 mg, 0.075 mmol) and boric acid (5.0 mg, 0.081 mmol) were added at room temperature (25° C.) and the mixture was stirred for 5 min. To this mixture, compound 7ba (50.0 mg, 0.074 mmol) was added and the mixture was stirred at the same temperature for 48 h. The mixture was purified by silica gel flash column chromatography ($CH_2Cl_2$/MeOH=69:31 to 51:49) to give 8e (21.5 mg, 35%) as a pale yellow solid.

Rf=0.16 ($CH_2Cl_2$/MeOH=2:1). $^1$H NMR (400 MHz, $CD_3OD$): δ 7.99 (s, 1H), 7.82-7.72 (m, 3H), 7.80 (d, J=16.0 Hz, 1H), 7.25 (d, J=2.4 Hz, 1H), 7.16 (dd, J=8.8 Hz, 2.4 Hz, 129.1, 129.0, 105.0, 80.8, 80.4, 80.2, 80.0, 78.5, 77.9, 77.6, 77.1, 77.0, 74.84, 74.79, 74.76, 74.6, 72.52, 72.48, 70.3, 62.49, 62.46, 62.0, 61.6, 41.6, 34.7, 23.9, 21.5, 17.2. HRMS (ESI): calcd for $C_{22}H_{35}O_{12}N_2S$ ([M+H]$^+$) 551.1905, found 551.1871.

Compound 10

A mixture of 7aa (100 mg, 0.148 mmol) and (aminooxy)acetic acid hemihydrochloride ($H_2N$—O—$CH_2COOH$•½HCl) (24.0 mg, 0.220 mmol) in DMSO (1.0 mL) was stirred at room temperature (25° C.) for 18 h. The mixture was purified by silica gel flash column chromatography ($CH_2Cl_2$/MeOH=54:46 to 26:74) to give the corresponding oxime ether derivative (110 mg, 99%). A mixture of the oxime ether (100 mg, 0.134 mmol), dansylcadaverine (49.0 mg, 0.146 mmol), and 4-(4,6-dimethoxy-1,3,5-triazin-2-yl)-4-methylmorpholinium chloride (56.0 mg, 0.200 mmol) in MeOH (1.0 mL) was stirred at room temperature (25° C.) for 18 h. The mixture was purified by silica gel flash column chromatography (CH$_2$Cl$_2$/MeOH=82:18 to 50:50) to give 10 (81.8 mg, 57%) as a pale yellow solid.

Rf=0.38 (CH$_2$Cl$_2$/MeOH (3:1). $^1$H NMR (400 MHz, CD$_3$OD): δ 8.55 (d, J=8.8 Hz, 1H), 8.36 (d, J=8.4 Hz, 1H), 8.19 (dd, J=7.2 Hz, 0.8 Hz, 1H), 7.62-7.55 (m, 2H), 7.27 (d, J=7.6 Hz, 1H), 4.44 (d, J=8.0 Hz, 1H×⅓), 4.43 (d, J=8.0 Hz, 1H×⅔), 4.39 (s, 2H×⅔), 4.38 (s, 2H×⅓), 4.08-4.03 (m, 1H), 3.95-3.92 (m, 1H), 3.90-3.46 (m, 16H+1H×⅓), 3.46-3.39 (m, 1H×⅔), 3.34-3.30 (m, 1H), 3.18-3.11 (m, 1H), 3.09-3.00 (m, 2H), 2.95 (dd, J=14.4 Hz, 3.2 Hz, 1H×⅓), 2.88 (s, 6H), 2.88-2.80 (m, 3H), 2.71 (dd, J=14.4 Hz, 2.8 Hz, 1H×⅔), 2.58 (dd, J=14.4 Hz, 8.8 Hz, 1H×⅓), 2.28 (dd, J=14.4 Hz, 9.2 Hz, 1H×⅔), 2.01 (s, 3H), 1.96 (s, 3H×⅔), 1.90 (s, 3H×⅓), 1.78-1.70 (m, 1H), 1.38-1.25 (m, 4H), 1.20-1.10 (m, 2H). $^{13}$C NMR (100 MHz, CD$_3$OD) δ 175.5, 174.9, 172.5, 172.4, 160.3, 160.2, 153.2, 137.2, 131.2, 131.1, 131.0, 130.1, 129.1, 124.3, 120.6, 116.4, 105.1, 101.1, 81.4, 80.22, 80.17, 78.5, 78.2, 77.9, 77.6, 77.0, 75.5, 75.1, 74.9, 73.1, 73.0, 72.9, 70.8, 70.1, 69.3, 69.0, 64.6, 62.7, 62.3, 54.0, 45.8, 43.7, 42.1, 39.8, 39.7, 30.1, 29.8, 24.7, 22.6, 20.7, 15.1. HRMS (ESI): calcd for C$_{45}$H$_{70}$N$_5$O$_{22}$S ([M+H]$^+$) 1064.4228, found 1064.4231.

INDUSTRIAL APPLICABILITY

The present invention can provide novel oligosaccharide C-glycoside derivatives which are biologically important under high stereoselective, mild, atom-economical condition.

This application claims the benefit of U.S. Provisional Patent Application No. 62/647,241, filed Mar. 23, 2018, the disclosure of which is incorporated by reference herein in its entirety.

The invention claimed is:

1. A process for preparing a compound of formula I

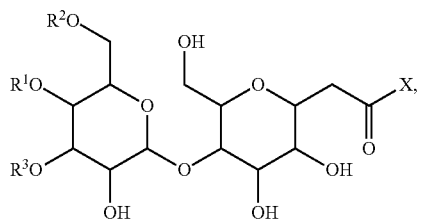

wherein the compound of formula I is a single diastereomer of the following β-anomer:

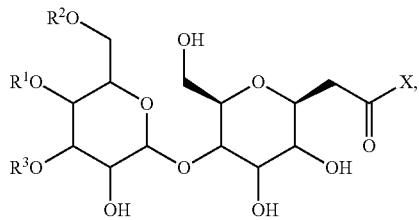

or an amount of the β-anomer to an amount of an α-anomer (β-anomer:α-anomer) of the compound of formula I is >10:1, or a pharmaceutically acceptable salt thereof, the process comprising:
reacting a compound of formula II

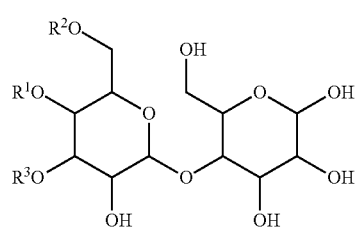

with a compound of formula III

wherein
X is C$_{1-7}$alkyl, C$_{3-7}$cycloalkyl, halo-C$_{1-7}$alkyl, C$_{1-7}$alkoxy, halo-C$_{1-7}$alkoxy, C$_{1-7}$alkoxy-C$_{1-7}$alkyl, (C$_{1-7}$alkoxycarbonyl)-C$_{1-7}$alkyl, C$_{2-7}$alkynyl-C$_{1-7}$alkyl, or aryl, which are optionally substituted,
R$^1$ is H, or a sugar residue,
R$^2$ is H, or a sugar residue, and
R$^3$ is H, or a sugar residue,
in the presence of at least one primary or secondary amine and at least one additive selected from the group consisting of:
(a) pyrrolidine and H$_3$BO$_3$,
(b) pyrrolidine and B(OMe)$_3$, and
(c) benzylamine and H$_3$BO$_3$,
to prepare the compound of formula I.

2. The process according to claim 1, wherein the compound of formula I is selected from the group consisting of:

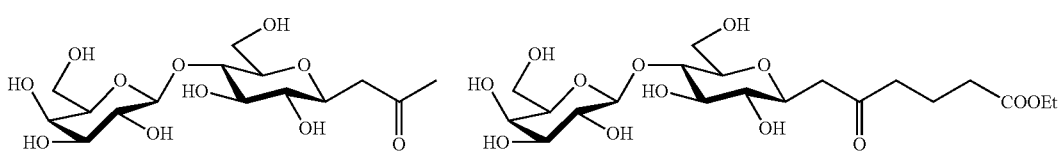

-continued
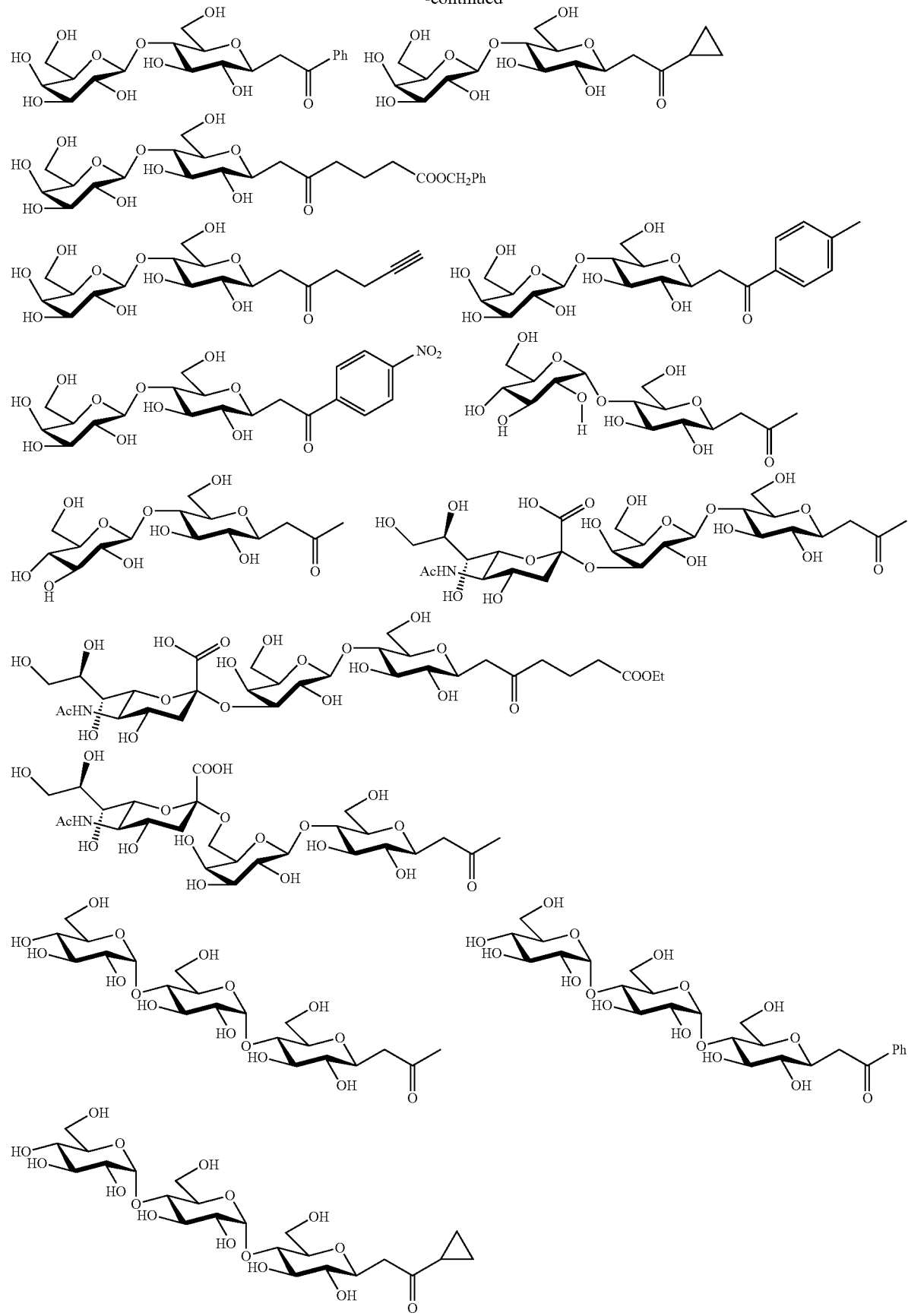

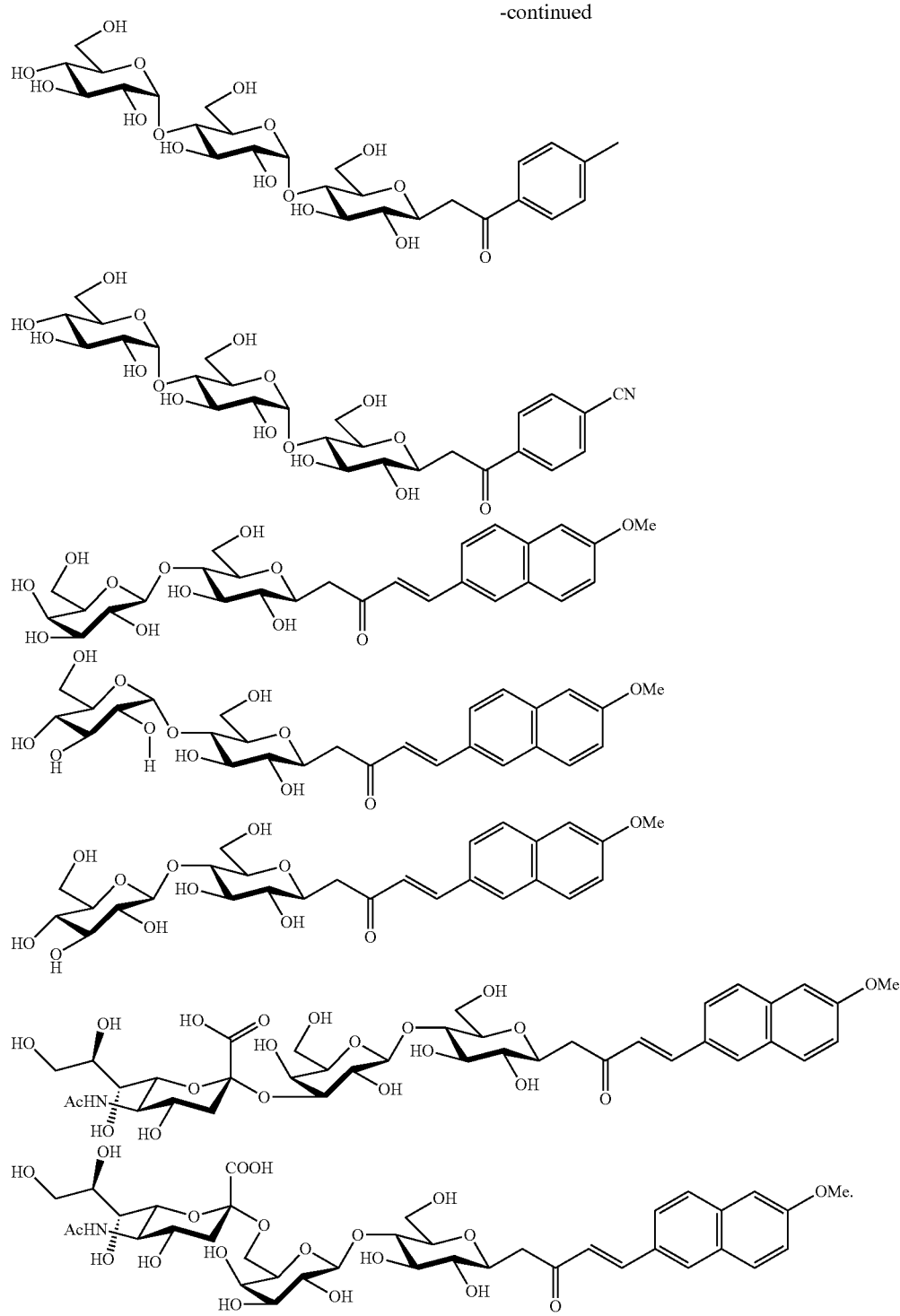
3. The process according to claim 1, wherein the amount of the β-anomer to the amount of the α-anomer (β-anomer: α-anomer) of the compound of formula I is >20:1.
4. The process according to claim 1, further comprising mixing the compound of formula I or a pharmaceutically acceptable salt thereof, with a pharmaceutically acceptable carrier to prepare a pharmaceutical composition.

5. A process for preparing a compound of I-1

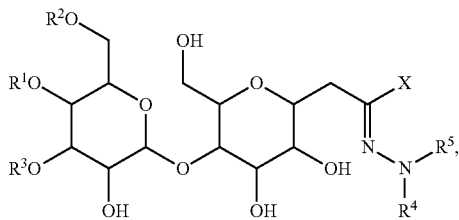  I-1 wherein the compound of formula I-1 is a single diastereomer of the following β-anomer:

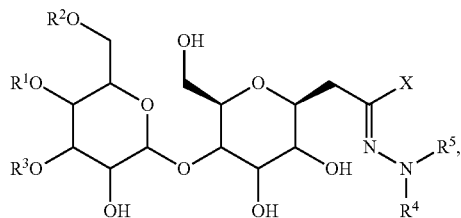

or an amount of the β-anomer to an amount of an α-anomer (β-anomer:α-anomer) of the compound of formula I-1 is >10:1,
or a pharmaceutically acceptable salt thereof,
the process comprising:
reacting a compound of formula II

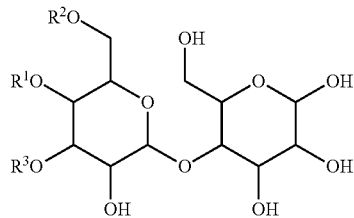  II with a compound of formula III

  III in the presence of at least one primary or secondary amine and at least one additive selected from the group consisting of:
(a) pyrrolidine and $H_3BO_3$,
(b) pyrrolidine and $B(OMe)_3$, and
(c) benzylamine and $H_3BO_3$,
to give a compound of formula I

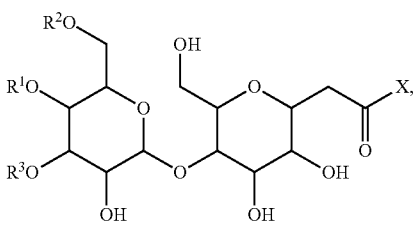  I wherein the compound of formula I is a single diastereomer of the following β-anomer:

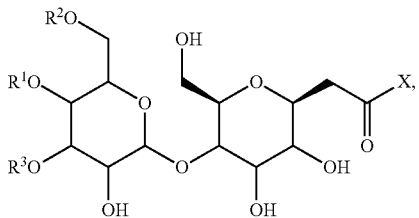

or an amount of the β-anomer to an amount of an α-anomer (β-anomer:α-anomer) of the compound of formula I is >10:1, and
reacting the compound of formula I with a reactant to prepare the compound of I-1, wherein
X is $C_{1-7}$alkyl, $C_{3-7}$cycloalkyl, halo-$C_{1-7}$alkyl, $C_{1-7}$alkoxy, halo-$C_{1-7}$alkoxy, $C_{1-7}$alkoxy-$C_{1-7}$alkyl, ($C_{1-7}$alkoxycarbonyl)-$C_{1-7}$alkyl, $C_{2-7}$alkynyl-$C_{1-7}$alkyl, or aryl, which are optionally substituted,
$R^1$ is H, or a sugar residue,
$R^2$ is H, or a sugar residue, and
$R^3$ is H, or a sugar residue,
$R^4$ and $R^5$ independently from each other are selected from the group consisting of H, $C_{1-7}$alkyl, phenyl, benzyl, piperidinyl, p-tosyl, and 1-phthalazinyl, wherein the $C_{1-7}$alkyl, phenyl, benzyl, piperidinyl, p-tosyl, and 1-phthalazinyl are optionally substituted.

6. The process according to claim 5, further comprising mixing the compound of formula I-1 or a pharmaceutically acceptable salt thereof, with a pharmaceutically acceptable carrier to prepare a pharmaceutical composition.

* * * * *